United States Patent
Jonsson et al.

(10) Patent No.: US 11,540,929 B2
(45) Date of Patent: *Jan. 3, 2023

(54) TAPERED FLEX PLATE FOR PROSTHETIC FOOT

(71) Applicant: Össur Iceland ehf, Reykjavik (IS)

(72) Inventors: Orn Ingvi Jonsson, Reykjavik (IS); Aron Kristbjorn Albertsson, Hafnarfjordur (IS)

(73) Assignee: Össur Iceland ehf, Reykjavik (IS)

( * ) Notice: Subject to any disclaimer, the term of this patent is extended or adjusted under 35 U.S.C. 154(b) by 137 days.

This patent is subject to a terminal disclaimer.

(21) Appl. No.: 16/934,381

(22) Filed: Jul. 21, 2020

(65) Prior Publication Data

US 2021/0000618 A1    Jan. 7, 2021

Related U.S. Application Data

(63) Continuation of application No. 15/952,838, filed on Apr. 13, 2018, now Pat. No. 10,751,200, which is a
(Continued)

(51) Int. Cl.
*A61F 2/66*    (2006.01)

(52) U.S. Cl.
CPC .............. *A61F 2/66* (2013.01); *A61F 2/6607* (2013.01); *A61F 2002/6614* (2013.01);
(Continued)

(58) Field of Classification Search
CPC ... A61F 2/66; A61F 2/6607; A61F 2002/6671
See application file for complete search history.

(56) References Cited

U.S. PATENT DOCUMENTS

| 5,116,384 A | 5/1992 | Wilson et al. |
| 5,728,171 A | 3/1998 | Bryant, Jr. et al. |

(Continued)

FOREIGN PATENT DOCUMENTS

| CN | 101094628 A | 12/2007 |
| WO | WO 2010/002744 A1 | 1/2010 |

(Continued)

OTHER PUBLICATIONS

Rusaw et al., "Sagittal plane position of the functional joint centre of prosthetic foot/ankle mechanisms," Clinical Biomechanics 25, 2010, pp. 713-720.

(Continued)

*Primary Examiner* — Bruce E Snow
(74) *Attorney, Agent, or Firm* — Knobbe, Martens, Olson & Bear, LLP

(57) ABSTRACT

Prosthetic feet that provide improved rollover and performance are provided. A prosthetic foot can include a lower foot member extending from a heel end to a toe end, a second foot member disposed above the lower foot member, and an optional third foot member disposed above the second foot member. The second foot member is tapered such that its thickness decreases toward the proximal end. Optionally, the second foot member can taper toward its distal end as well as toward its proximal end from an intermediate location on the second foot member. The third foot member can be tapered such that its thickness decreases toward the distal end. There can be a gap between a distal end of the third foot member and the second foot member that closes during dorsiflexion of the prosthetic foot during use and provides dynamic stiffness control to the prosthetic foot.

20 Claims, 25 Drawing Sheets

Related U.S. Application Data continuation of application No. 15/139,047, filed on Apr. 26, 2016, now Pat. No. 9,968,467.

(60) Provisional application No. 62/153,406, filed on Apr. 27, 2015.

(52) U.S. Cl.
CPC ............ *A61F 2002/6621* (2013.01); *A61F 2002/6642* (2013.01); *A61F 2002/6657* (2013.01); *A61F 2002/6664* (2013.01); *A61F 2002/6671* (2013.01); *A61F 2230/0041* (2013.01)

(56) References Cited

U.S. PATENT DOCUMENTS

| | | | |
|---|---|---|---|
| 5,993,488 | A | 11/1999 | Philips |
| 6,029,374 | A | 2/2000 | Herr et al. |
| 6,929,665 | B2 * | 8/2005 | Christensen ............ A61F 2/66 623/55 |
| 7,611,543 | B2 | 11/2009 | Townsend et al. |
| 8,007,544 | B2 | 8/2011 | Jonsson et al. |
| 9,017,421 | B2 * | 4/2015 | Lecomte ............... A61F 2/66 623/53 |
| 9,439,786 | B2 * | 9/2016 | Nijman ................ A61F 2/66 |
| 9,968,467 | B2 | 5/2018 | Jonsson et al. |
| 10,751,200 | B2 | 8/2020 | Jonsson et al. |
| 2004/0068328 | A1 | 4/2004 | Christensen |
| 2004/0225376 | A1 | 11/2004 | Townsend et al. |
| 2006/0178754 | A1 | 8/2006 | Townsend et al. |
| 2008/0183301 | A1 * | 7/2008 | Christensen ............ A61F 2/70 623/53 |
| 2012/0179274 | A1 * | 7/2012 | Christensen ............ A61F 2/66 623/55 |
| 2013/0261767 | A1 | 10/2013 | Kranner et al. |
| 2014/0228974 | A1 | 8/2014 | Lecomte et al. |
| 2016/0199202 | A1 | 7/2016 | Jonasson et al. |

FOREIGN PATENT DOCUMENTS

| | | |
|---|---|---|
| WO | WO 2012/009319 A2 | 1/2012 |
| WO | WO 2016/176220 A1 | 11/2016 |

OTHER PUBLICATIONS

Freedom Innovations, LLC "Thrive The World's First Load-Activated Prosthetic Foot," 2010, in 3 pages.

Ohio Willow Wood Trailblazer™ product, http://www.willowwoodco.com/products-and-services/feet/high-activity/trailblazer, believed to have been available more than one year before Apr. 27, 2015.

Orthocare Magellan product, believed to have been available more than one year before Apr. 27, 2015.

Fillauer Element™ product, Fillauer Companies Prosthetic Product Information Guide, Feb. 2011.

Fillauer Wave Comfort Foot System™ Information Sheet, http://www.fillauer.com/pdf/AD315-Wave-Comfort-Foot-System.pdf, Sep. 1, 2011.

International Search Report and Written Opinion in corresponding International Patent Application No. PCT/US2016/029391, dated Oct. 4, 2016, in 20 pages.

Office Action in corresponding Chinese Patent Application No. 201680026366.3, dated Dec. 27, 2018, in 5 pages.

Office Action in corresponding Chinese Patent Application No. 201680026366.3, dated Aug. 26, 2019, in 15 pages.

Office Action in corresponding Chinese Patent Application No. 201680026366.3, dated Mar. 13, 2020, in 9 pages.

* cited by examiner

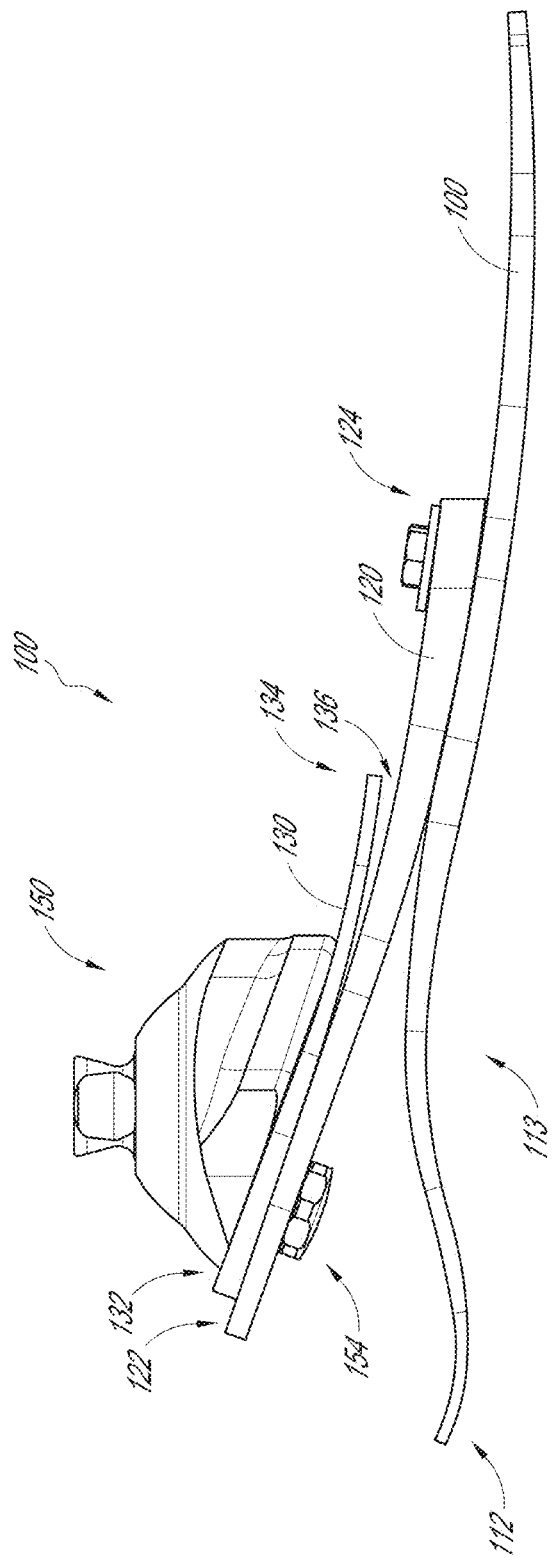

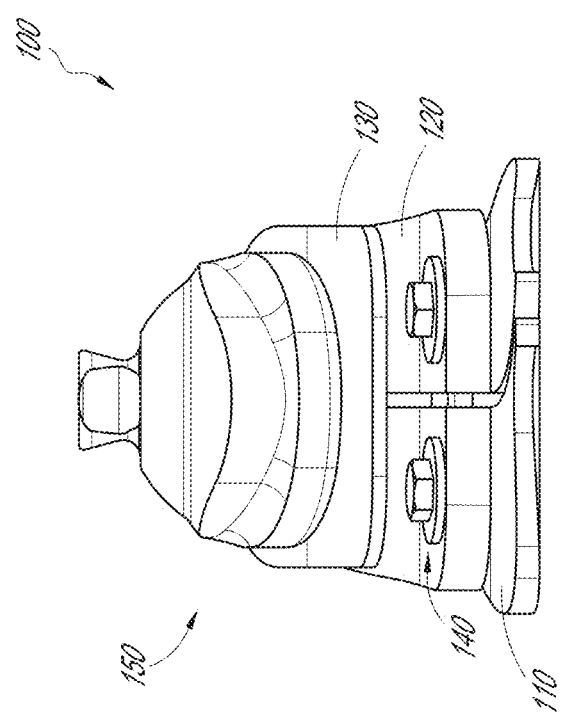

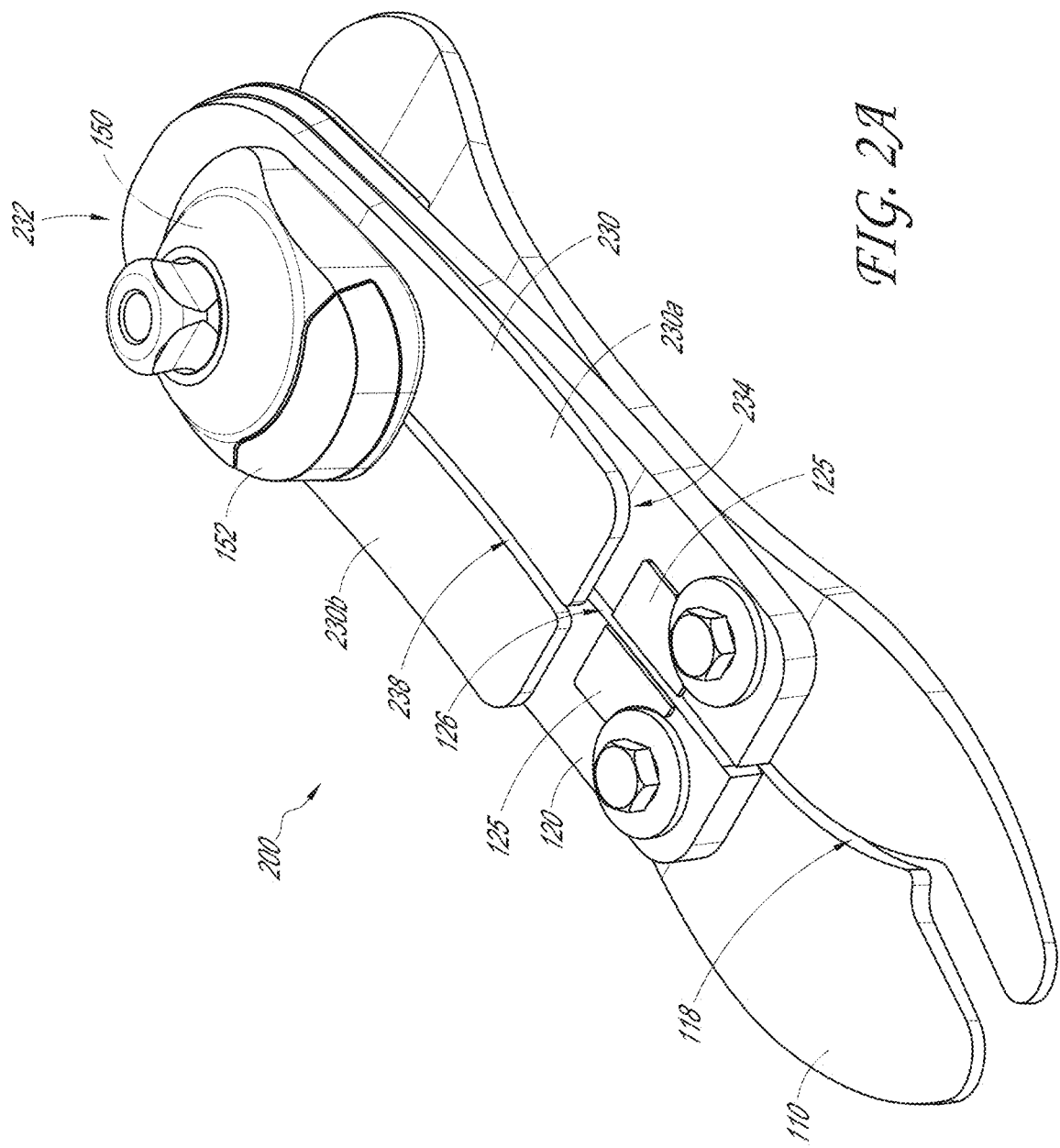

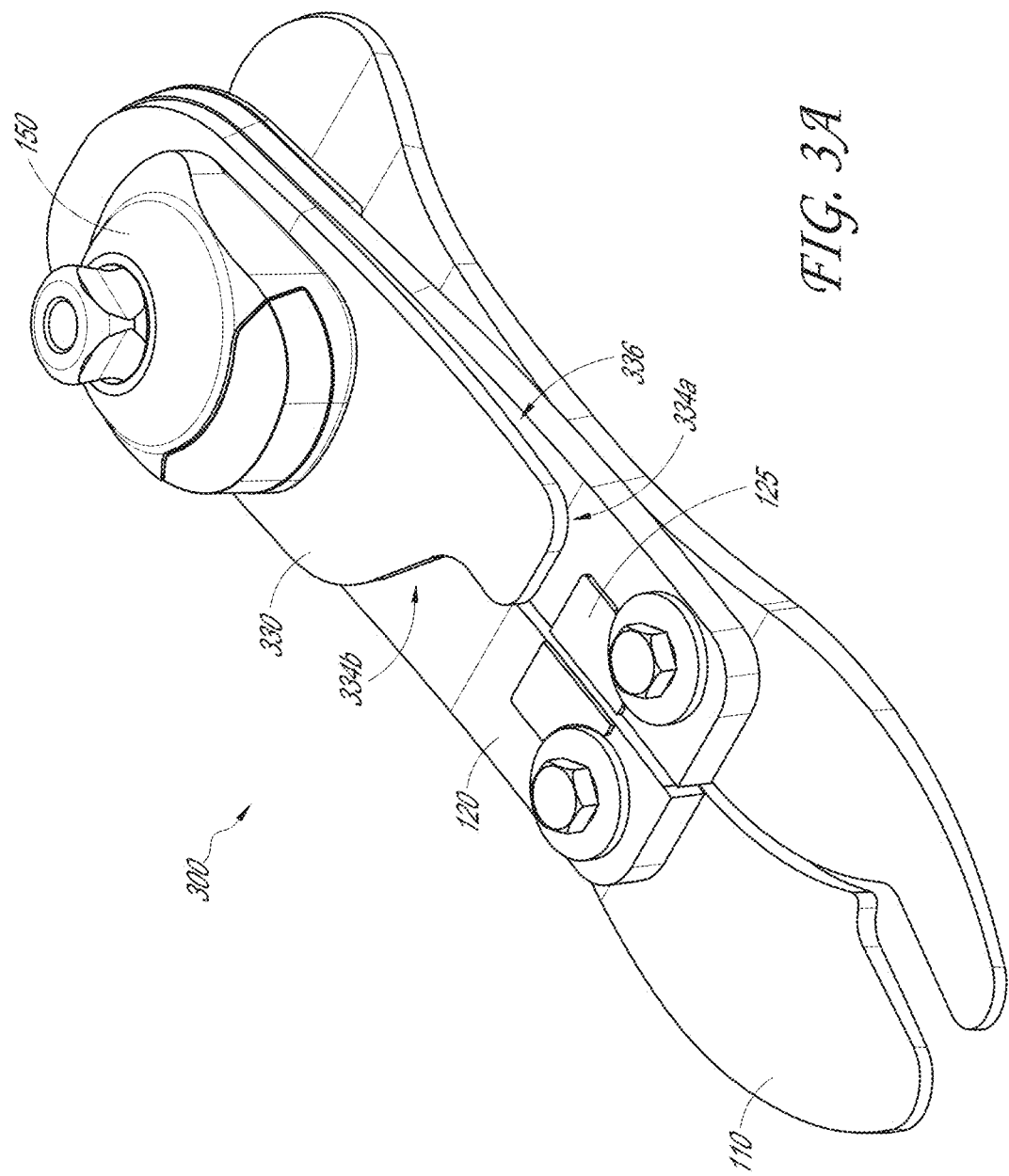

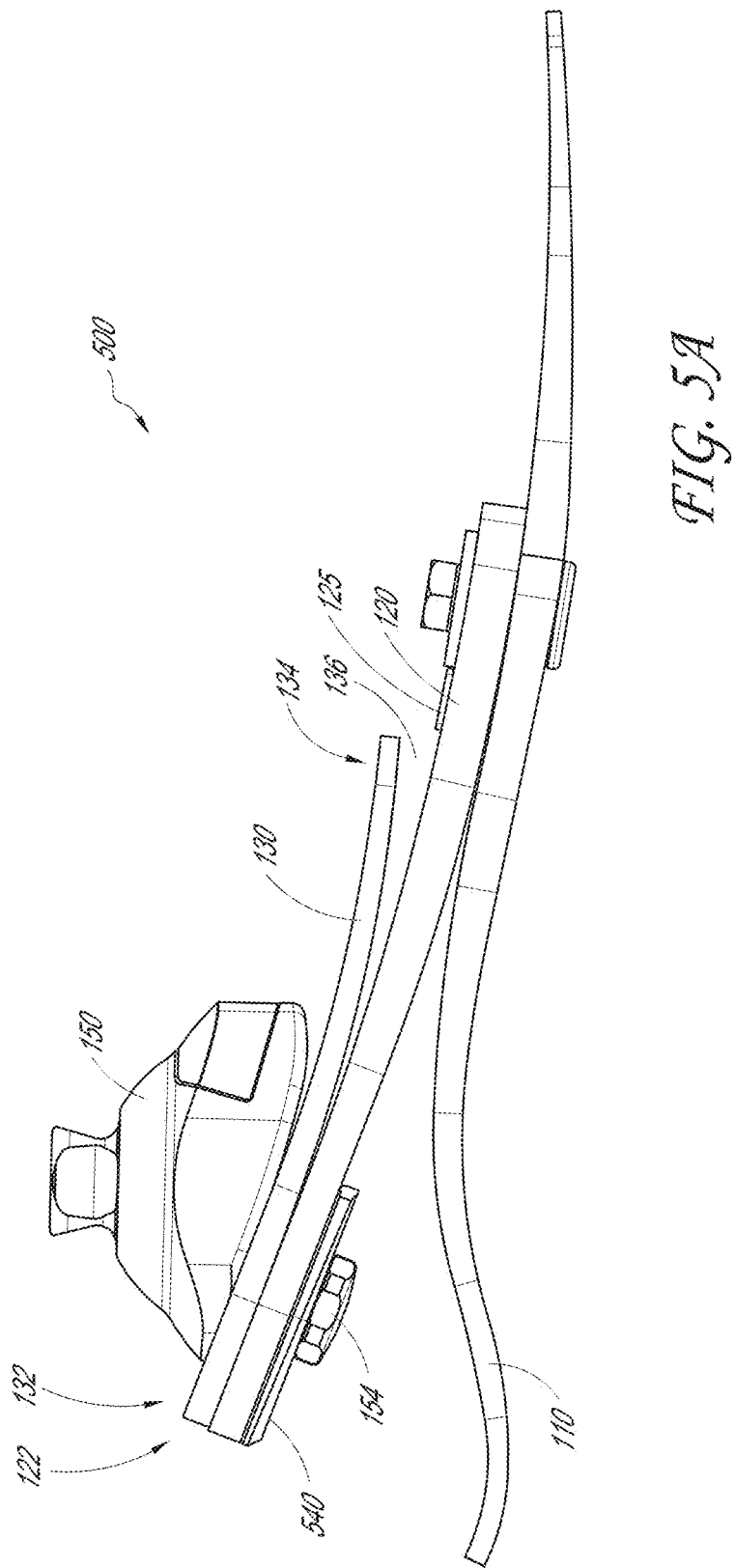

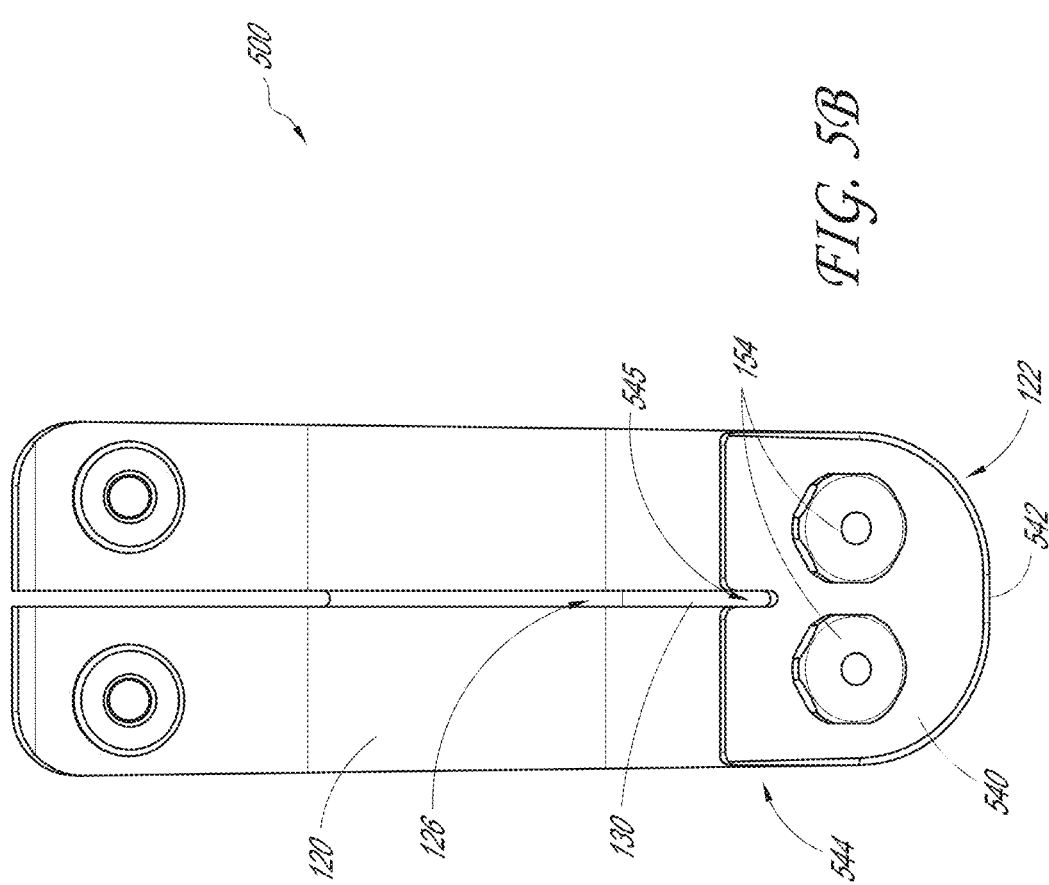

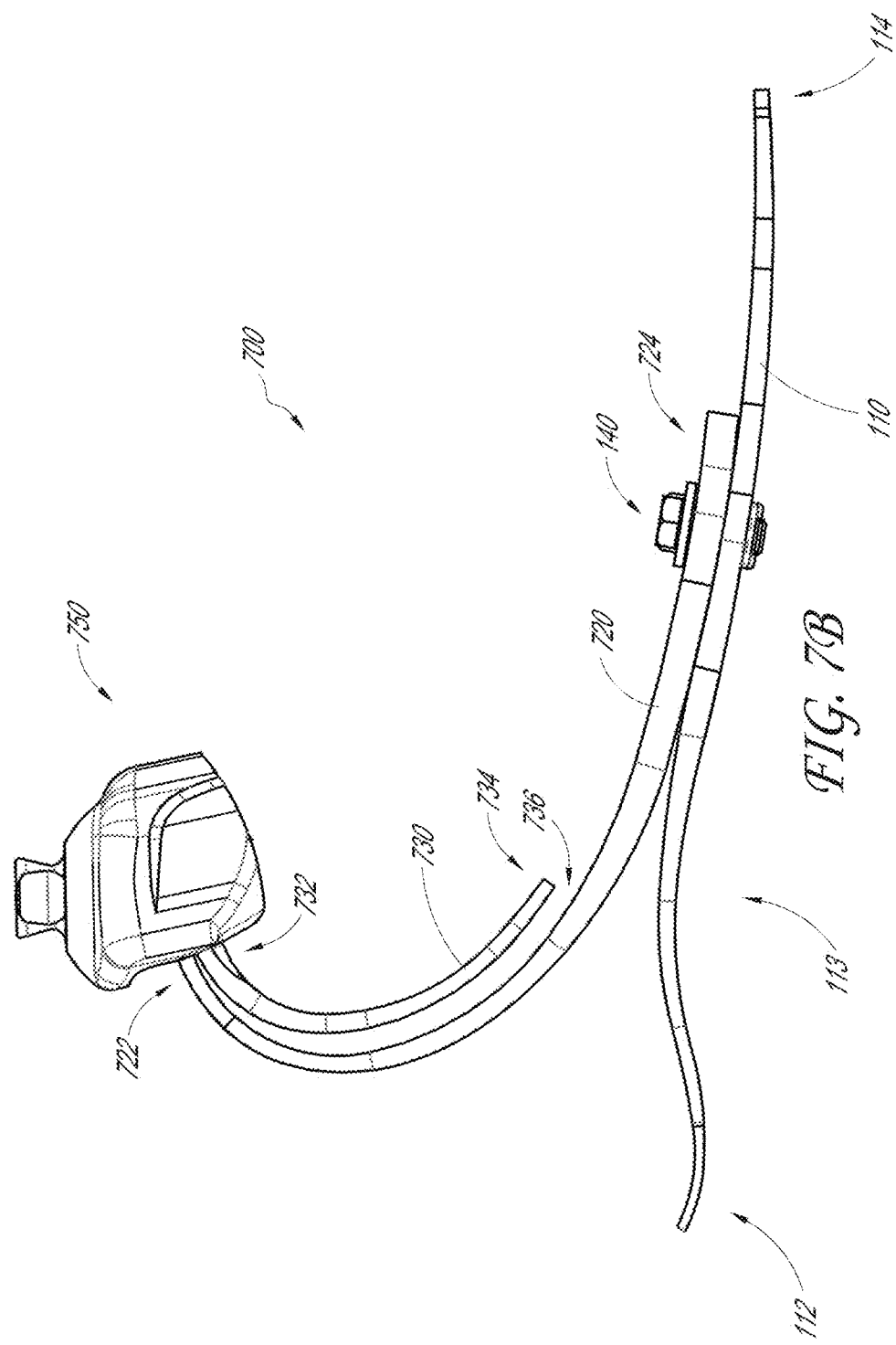

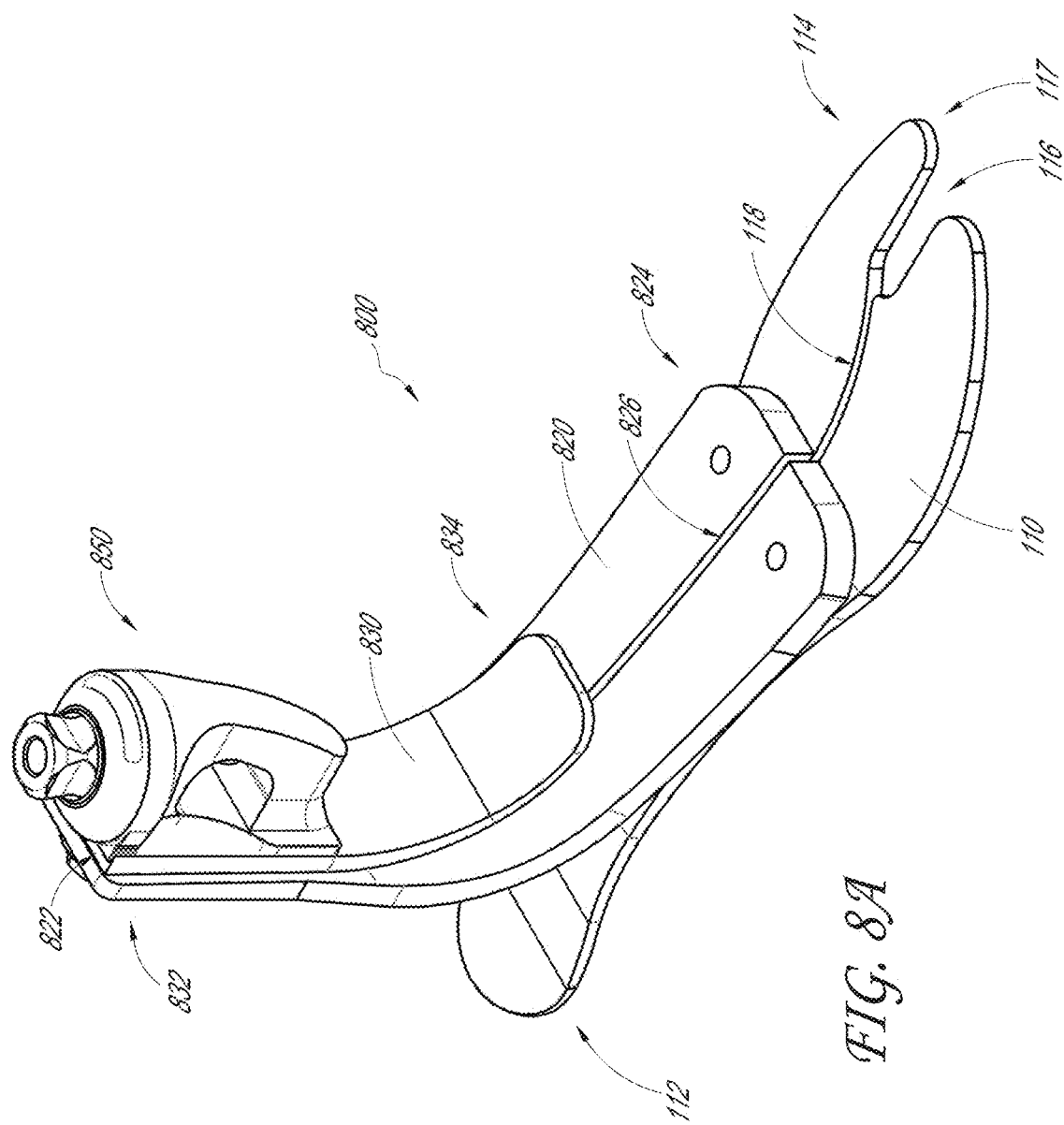

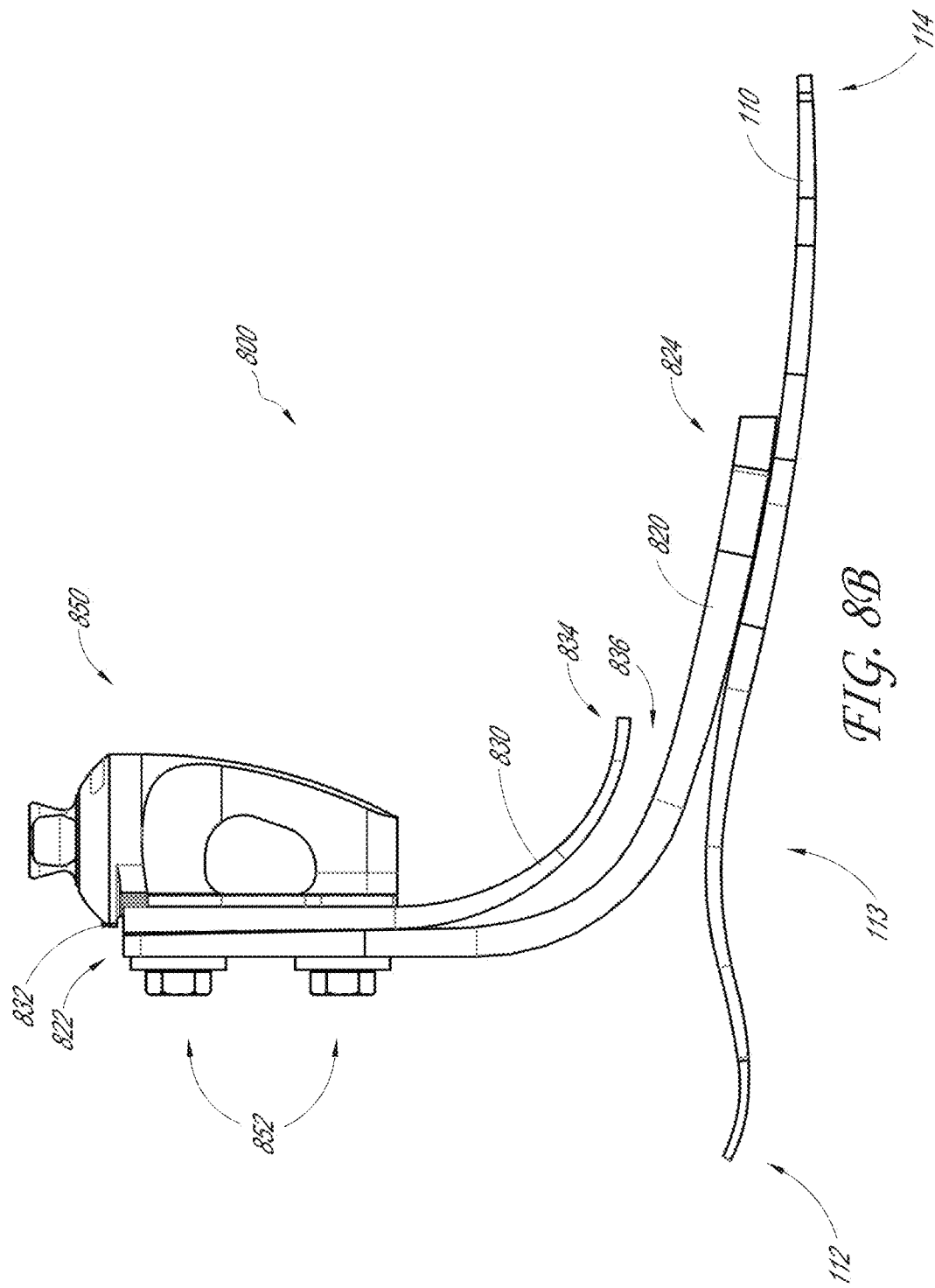

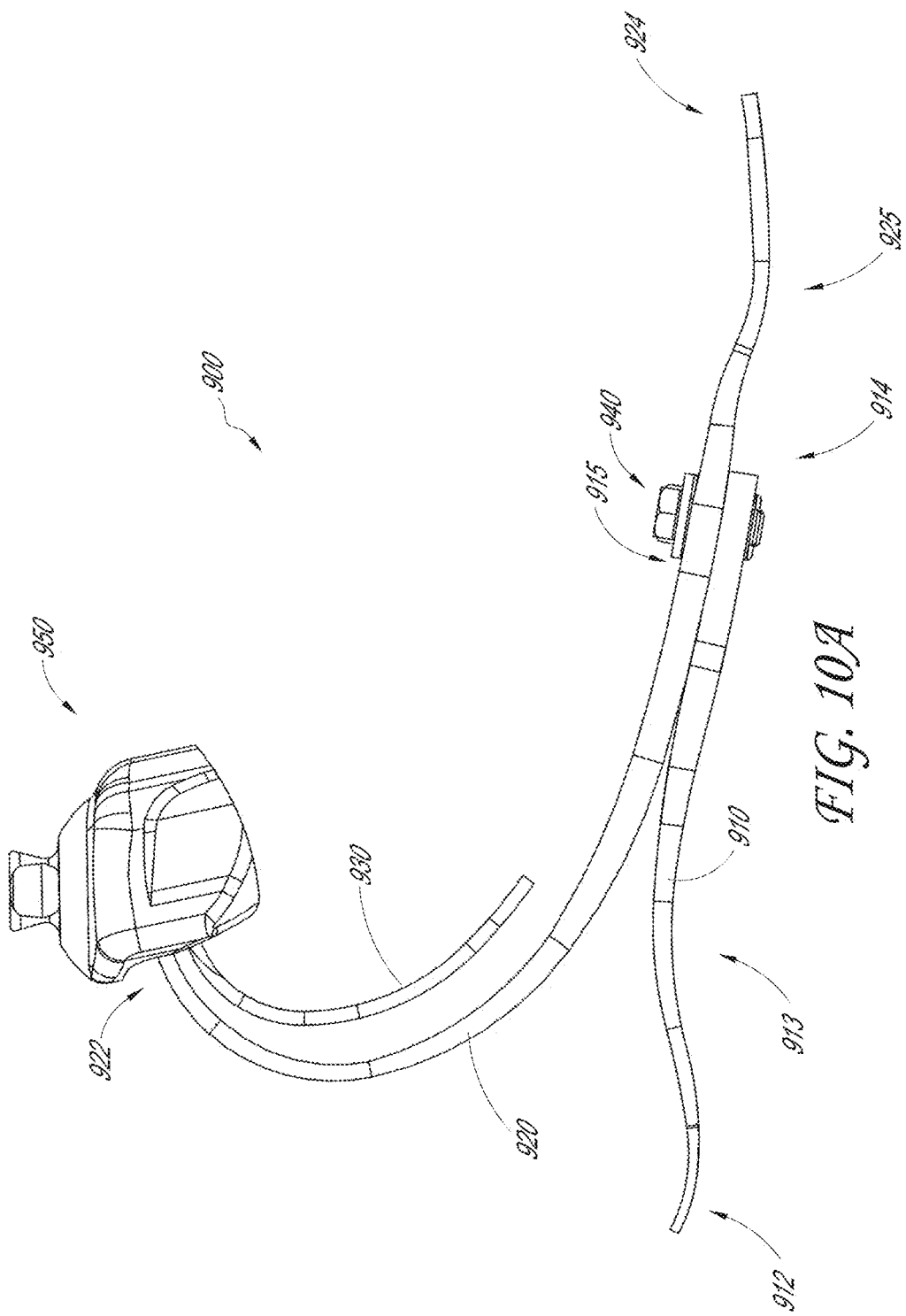

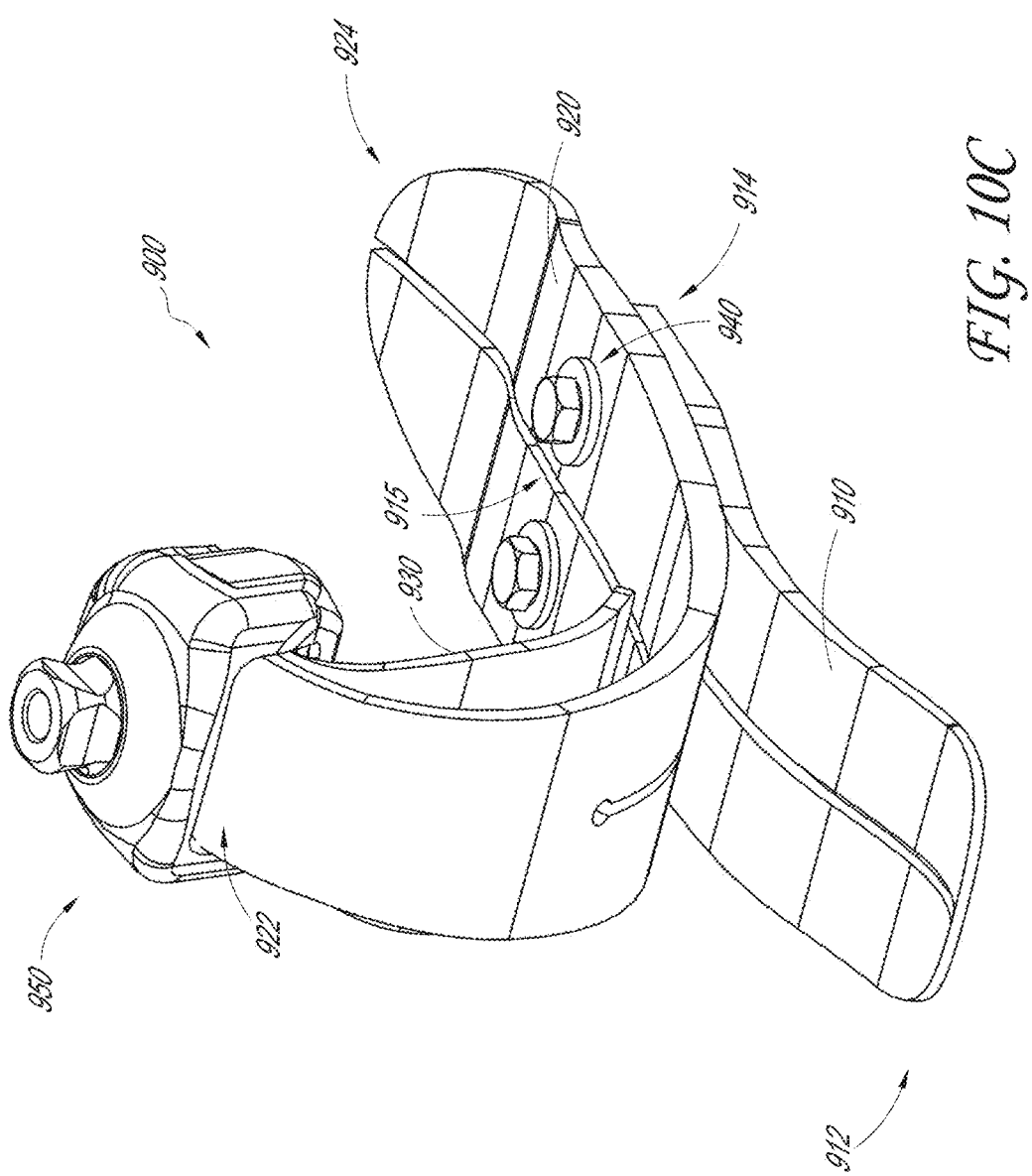

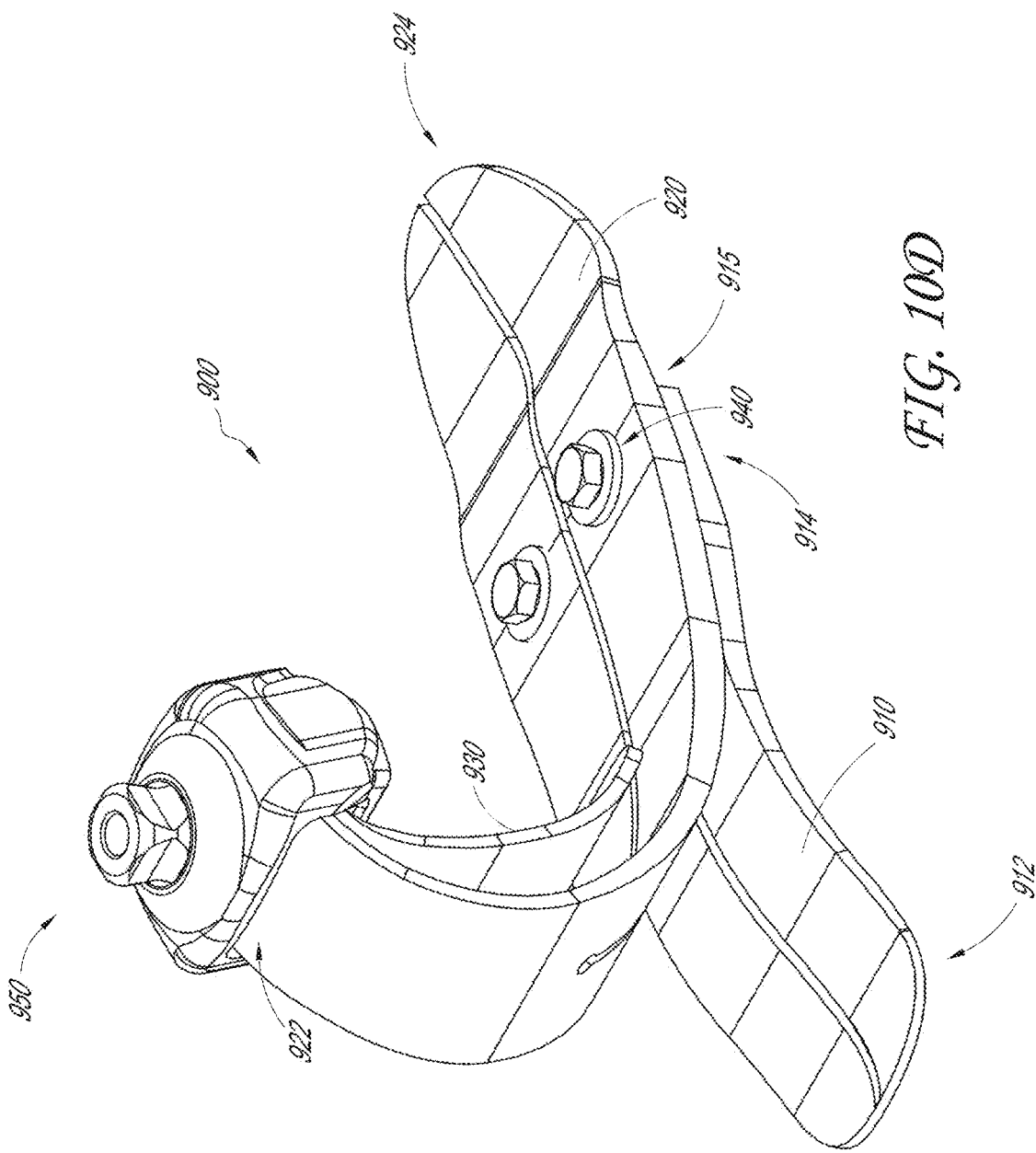

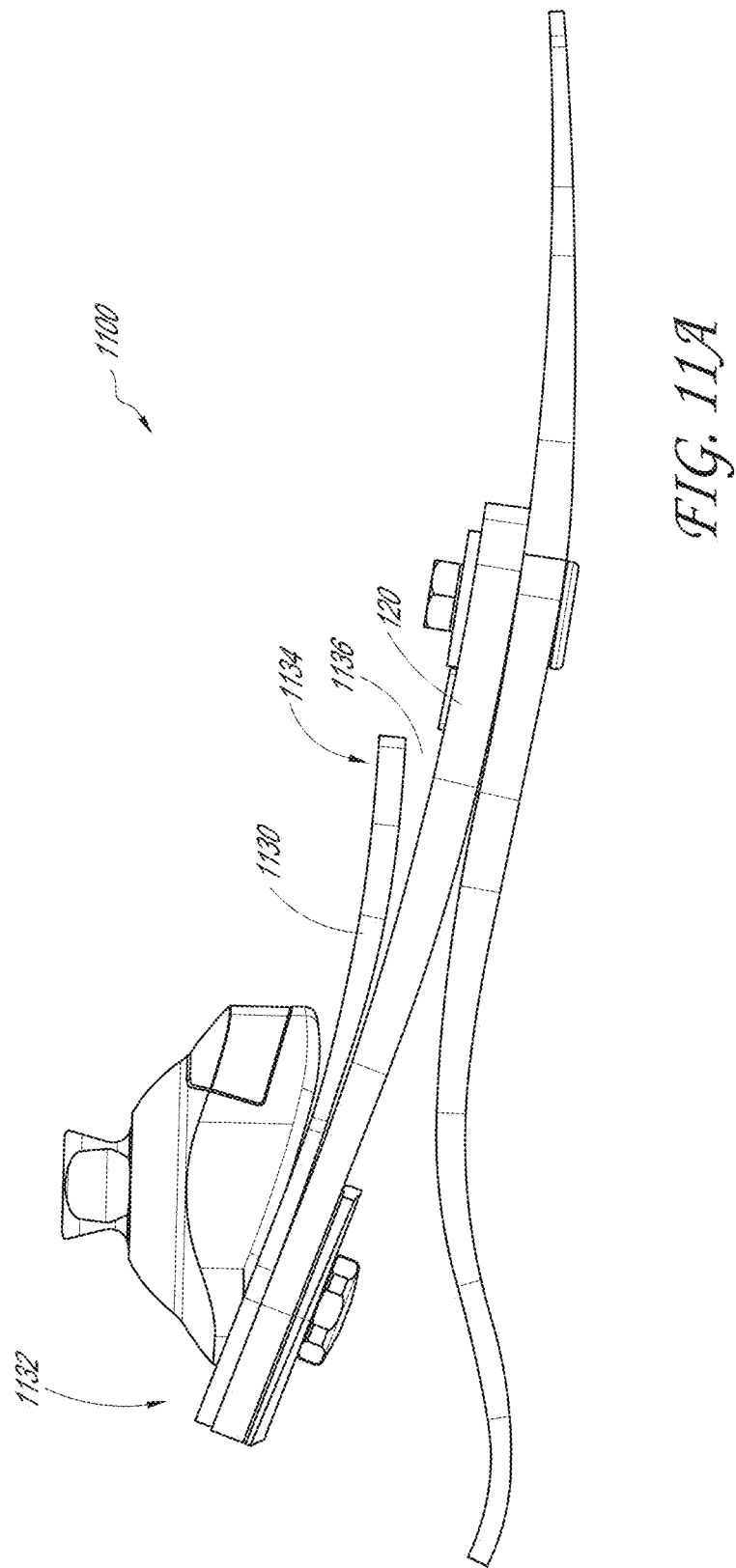

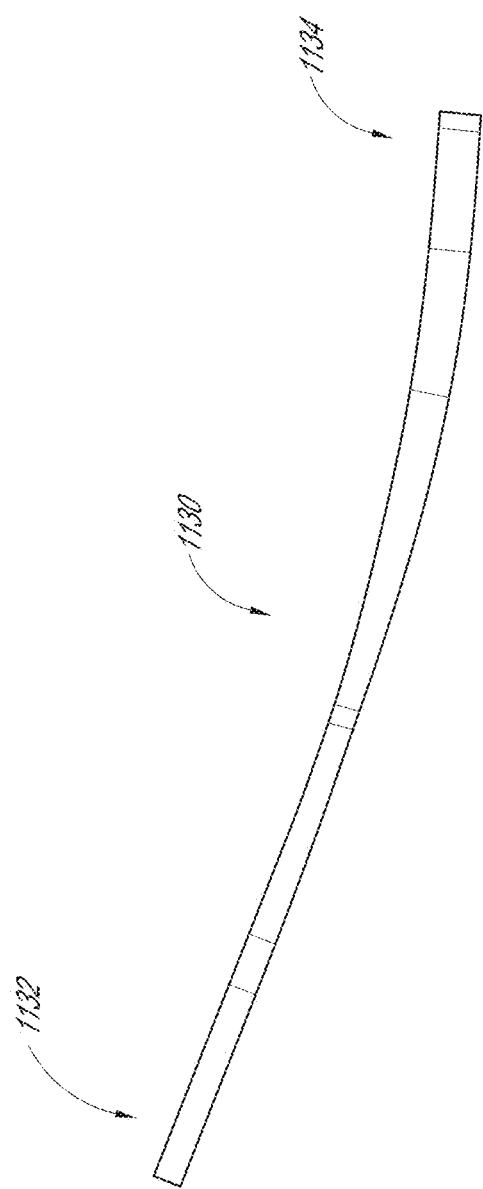

TAPERED FLEX PLATE FOR PROSTHETIC FOOT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 15/952,838, filed Apr. 13, 2018, now U.S. Pat. No. 10,751,200, which is a continuation of U.S. application Ser. No. 15/139,047, filed Apr. 26, 2016, now U.S. Pat. No. 9,968,467, which claims the priority benefit of U.S. Provisional Application No. 62/153,406, filed Apr. 27, 2015, the entirety of which is incorporated herein by reference.

BACKGROUND

Field

The present disclosure relates generally to prosthetic feet. In some embodiments, the present disclosure relates more specifically to prosthetic feet having characteristics that provide improved rollover and/or performance.

Description of the Related Art

Various types of prosthetic foot and cosmesis devices are available as substitutes for human feet. Many prosthetic devices available today incorporate various features to try to better approximate the functioning of natural feet. For example, some prosthetic foot designs seek to provide improved foot rollover during use. However, existing prosthetic feet often have centers of rotation positioned lower and/or more anteriorly than the typical center of rotation of a natural human foot and ankle.

SUMMARY

In some embodiments, prosthetic feet according to the present disclosure have a center of rotation that is closer to that of a natural human foot and/or more posterior than that of previously available prosthetic feet.

In some embodiments, a prosthetic foot includes an elongate lower foot member, and elongate intermediate foot member, and an elongate upper foot member. The lower foot member extends from a heel end to a toe end. The intermediate foot member extends from a proximal end to a distal end and is disposed above the lower foot member. The intermediate foot member is coupled to the lower foot member proximate the distal end of the intermediate foot member and proximal of the toe end of the lower foot member. The intermediate foot member includes a taper such that a thickness of the intermediate foot member increases toward the distal end of the intermediate foot member. The upper foot member extends from a proximal end to a distal end and is coupled to the intermediate foot member at or near the proximal ends of the intermediate foot member and upper foot member. The upper foot member is tapered such that a thickness of the upper foot member decreases toward the distal end of the upper foot member.

In some embodiments, the intermediate foot member is generally C-shaped. In some such embodiments, the upper foot member is also generally C-shaped. In other embodiments, the intermediate foot member is generally J-shaped. In some such embodiments, the upper foot member is also generally J-shaped. In some embodiments, a gap separates the distal end of the upper foot member from the intermediate foot member when the prosthetic foot is at rest on a support surface, and the gap closes during dorsiflexion to increase an amount of energy stored in the intermediate foot member as the prosthetic foot moves toward toe-off. The distal end of the upper foot member can engage the intermediate foot member during load to provide dynamic stiffness control. In some embodiments, the taper of the intermediate foot member shifts a center of rotation of the prosthetic foot rearward toward a location corresponding to a center of rotation of a natural human ankle.

In some embodiments, a prosthetic foot includes an elongate lower foot member and an elongate second foot member. The lower foot member extends from a heel end to a toe end. The second foot member extends from a proximal end to a distal end and is disposed above the lower foot member. The second foot member is coupled to the lower foot member proximate the distal end of the second foot member and proximal of the toe end of the lower foot member. The second foot member is tapered such that a thickness of the second foot member gradually increases toward the distal end of the second foot member.

In some embodiments, the prosthetic foot further includes an elongate upper foot member extending from a proximal end to a distal end and coupled to the second foot member at or near the proximal ends of the second foot member and upper foot member. In some such embodiments, the upper foot member is tapered such that a thickness of the upper foot member decreases toward the distal end of the upper foot member. A gap can separate the distal end of the upper foot member from the second foot member when the prosthetic foot is at rest on a support surface, and can close during dorsiflexion to increase an amount of energy stored in the second foot member as the prosthetic foot moves toward toe-off. The distal end of the upper foot member can engage the second foot member during load to provide dynamic stiffness control. In some embodiments, the taper of the second foot member shifts a center of rotation of the prosthetic foot rearward toward a location corresponding to a center of rotation of a natural human ankle.

In some embodiments, a prosthetic foot includes an elongate lower foot member extending from a proximal heel end to a distal end and an elongate second foot member extending from a proximal end to a distal toe end. The second foot member is disposed above the lower foot member and coupled to the lower foot member proximate the distal end of the lower foot member and proximal of the toe end of the second foot member. The second foot member is tapered such that a thickness of the second foot member gradually decreases from an intermediate location of the elongate foot member toward the proximal and distal toe ends of the second foot member.

In some embodiments, the prosthetic foot further includes an elongate upper foot member extending from a proximal end to a distal end and coupled to the second foot member at or near the proximal ends of the second foot member and upper foot member. The upper foot member can be tapered such that a thickness of the upper foot member decreases toward the distal end of the upper foot member. In some embodiments, a gap separates the distal end of the upper foot member from the second foot member when the prosthetic foot is at rest on a support surface, and wherein the gap closes during dorsiflexion to increase an amount of energy stored in the second foot member as the prosthetic foot moves toward toe-off. The distal end of the upper foot member can engage the second foot member during load to provide dynamic stiffness control. In some embodiments, the taper of the second foot member shifts a center of rotation of the prosthetic foot rearward toward a location corresponding to a center of rotation of a natural human ankle. The second foot member can be generally C-shaped. In some such embodiments, the upper foot member is also generally C-shaped. In some embodiments, the second foot member includes a change in curvature distal to the distal end of the lower foot member such that a toe portion of the second foot member is downwardly vertically offset from a remainder of the second foot member proximal to the change in curvature.

In some embodiments, a prosthetic foot includes an elongate foot member extending from a proximal end to a distal toe end, wherein the foot member is tapered such that a thickness of the foot member gradually decreases from an intermediate location of the elongate foot member toward the proximal and distal ends of the foot member. In some embodiments, the prosthetic foot further includes an adapter coupled to the proximal end of the foot member. In some embodiments, the foot further includes an elongate heel member extending from a proximal end to a distal end, wherein the foot member is disposed above the heel member and coupled to the heel member proximate the distal end of the heel member and proximal of the toe end of the foot member. In some embodiments, the foot also includes an elongate upper foot member extending from a proximal end to a distal end and disposed above and coupled to the elongate foot member at or near the proximal ends of the elongate foot member and upper foot member. The upper foot member can be tapered such that a thickness of the upper foot member decreases toward the distal end of the upper foot member. A gap can separate the distal end of the upper foot member from the foot member when the prosthetic foot is at rest on a support surface, and the gap can close during dorsiflexion to increase an amount of energy stored in the foot member as the prosthetic foot moves toward toe-off. In some embodiments, the distal end of the upper foot member engages the foot member during load to provide dynamic stiffness control.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 1B illustrates a side view of the prosthetic foot of FIG. 1A;

FIG. 1D illustrates a front view of the prosthetic foot of FIGS. 1A-1C;

FIG. 2A illustrates a perspective view of another example embodiment of a prosthetic foot.

FIG. 3A illustrates a perspective view of another example embodiment of a prosthetic foot.

FIG. 5A illustrates a side view of another example embodiment of a prosthetic foot.

FIG. 5B illustrates a bottom view of the prosthetic foot of FIG. 5A with a lower foot member.

FIG. 7B illustrates a side view of the prosthetic foot of FIG. 7A;

FIG. 8A illustrates a perspective view of another example embodiment of a prosthetic foot;

FIG. 8B illustrates a side view of the prosthetic foot of FIG. 8A;

FIGS. 10A-10D illustrate various views of another example embodiment of a prosthetic foot.

FIG. 11A illustrate a side view of another example embodiment of a prosthetic foot.

FIG. 11B illustrate a side view of an upper foot member of the prosthetic foot of FIG. 11A.

DETAILED DESCRIPTION

Figure 1A:
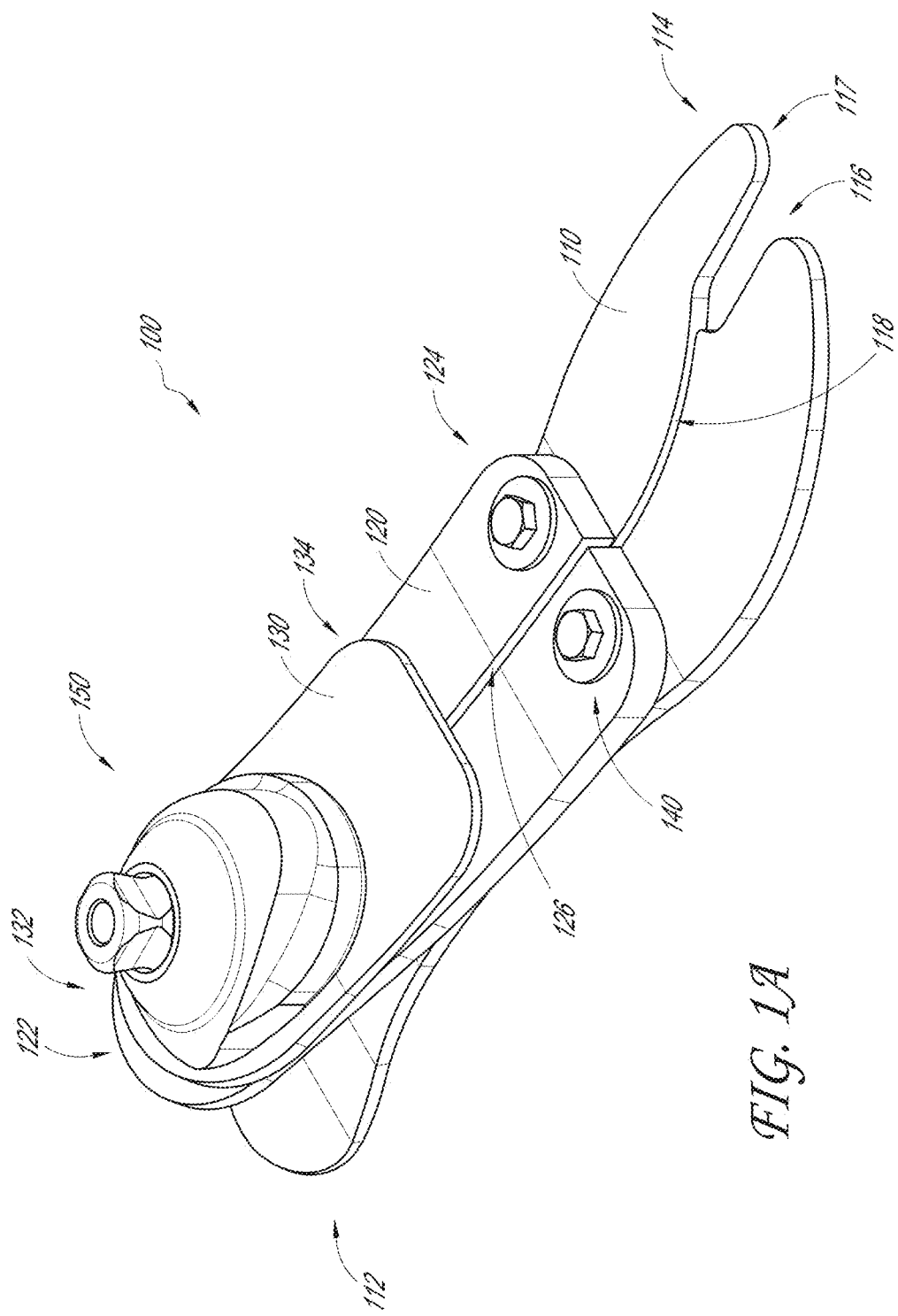
FIG. 1A illustrates a perspective view of an example embodiment of a prosthetic foot.
Figure 1C:
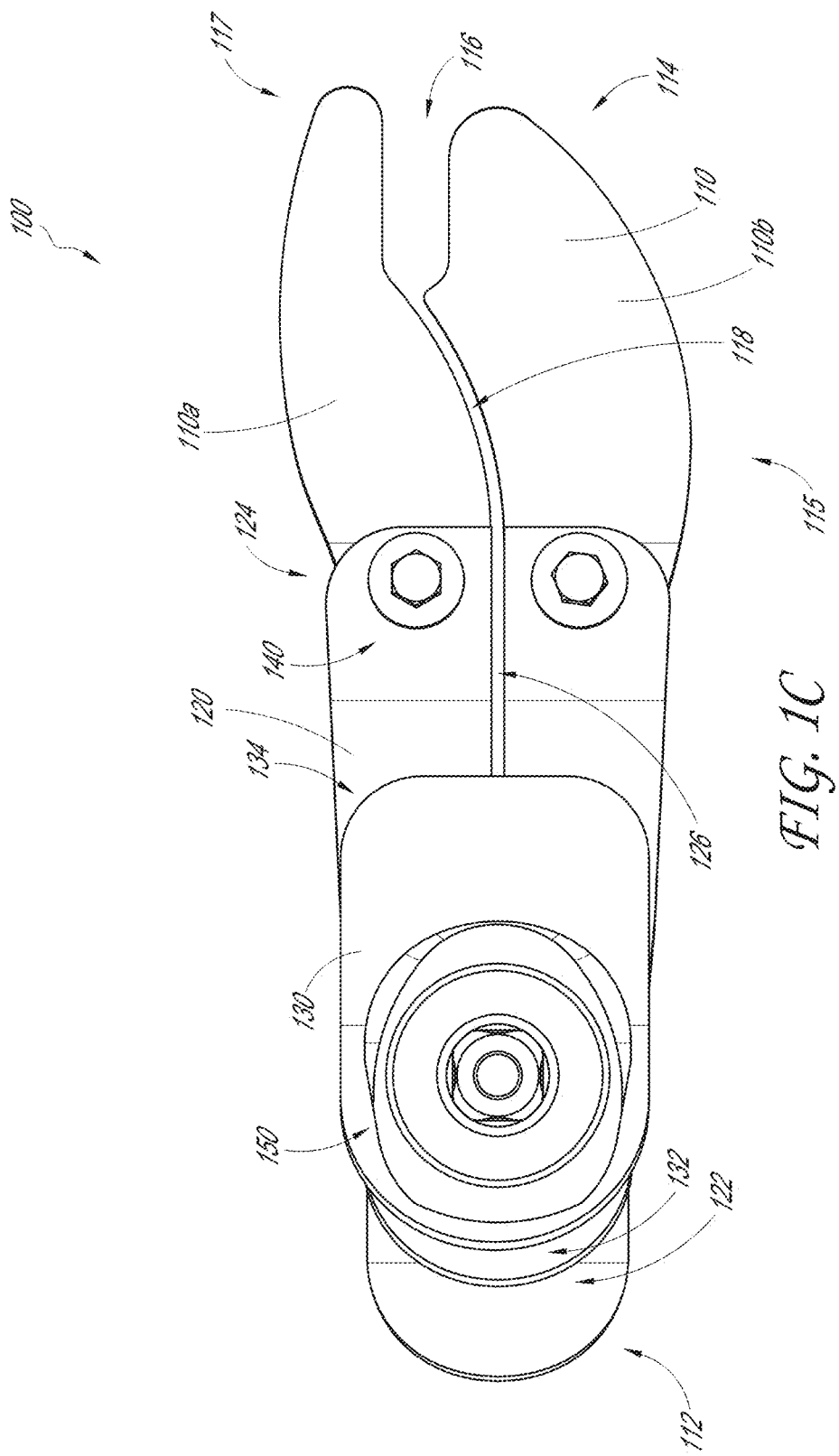
FIG. 1C illustrates a top view of the prosthetic foot of FIGS. 1A-1B.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

According to embodiments of the present disclosure, a prosthetic foot can include a lower foot member, a tapered intermediate foot member, and, optionally, an upper foot member, which can also be tapered. Prosthetic feet as described herein can also include an adapter configured to couple the foot to a user's residual limb (e.g., via a socket) or another prosthetic component (e.g., a pylon). FIGS. 1A-8B and 10A-10D illustrate various example embodiments of prosthetic feet 100, 200, 300, 400, 500, 600, 700, 800, 900 that can exhibit improved rollover and/or other performance characteristics in use. In some embodiments, the lower foot member is a heel-to-toe plate and extends beyond a distal end of the intermediate foot member. In other embodiments, the intermediate foot member can extend to a toe end, and the lower foot member can be a heel plate that extends from a heel end to a proximal end that is coupled to the intermediate foot member proximal to the toe end.

In the illustrated embodiments, the prosthetic feet 100, 200, 300, 400, 500, 600, 700, 800 include a lower foot member 110. Lower foot member 110 is substantially plate-like and has a generally rectangular or rectangular cross-section transverse to a longitudinal axis of the foot 100, 200, 300, 400, 500, 600, 700, 800 along at least a portion of its length. In some embodiments, the lower foot element 110 is constructed of a resilient material capable of flexing in multiple directions. The lower foot element 110 can include multiple layers or laminae. Examples of possible materials for the lower foot element 110 include carbon, any polymer material, and any composite of polymer and fiber. The polymer can be thermoset or thermoplastic. In a composite, the fiber reinforcement can be any type of fiber, such as carbon, glass, or aramid, or a combination of different types of fibers. The fibers can be long and unidirectional, or they can be chopped and randomly oriented.

The lower foot member 110 extends from a heel end 112 to a toe end 114 and includes an arch region 113 between the heel end 112 and the toe end 114, for example, at approximately the location of an arch of a natural human foot. The lower foot member 110 further includes a forefoot region 115 distal to the arch region 113 or between the arch region 113 and the toe end 114. In some embodiments, the forefoot region 115 is wider than the arch region 113 and/or heel end 112.

In some embodiments, a toe portion of the lower foot member 110 includes a generally U-shaped cut-out portion, slot, or gap 116 extending inwardly from the toe end 114. In some embodiments, the cut-out portion 116 is positioned toward a medial side of the longitudinal axis of the lower foot member 110, but is spaced from a medial edge of the lower foot member 110. The cut-out portion 116 gives the lower foot member 110 a "sandal toe" appearance and/or function and defines a structural "big toe" 117.

In the illustrated embodiments, the lower foot member 110 also includes a split 118 that at least partially extends substantially along the longitudinal axis of the foot. The split 118 provides a narrow gap between a medial portion or blade 110a and a lateral portion or blade 110b of the lower foot member 110 and allows the medial 110a and lateral 110b portions to flex somewhat independently of each other. As shown, in some embodiments, the split 118 does not extend to the heel end 112 of the lower foot member 110. In the illustrated embodiment, the split 118 extends substantially straight through the arch region 113, then curves medially in the forefoot region 115, or approximately at a border between the arch region 113 and the forefoot region 115, and extends to a base of the cut-out portion 116. Other configurations are also possible. Additional details regarding the lower foot member 110, alternative embodiments of a lower foot member, and other features and advantages can be found in U.S. Provisional Application No. 62/019,233, filed Jun. 30, 2014, the entirety of which is hereby incorporated herein by reference and should be considered a part of this specification.

As shown in FIGS. 1A-6B, the prosthetic foot 100, 200, 300, 400, 500, 600 also includes an intermediate foot member 120. The intermediate foot member 120 is substantially plate-like and has a generally rectangular or rectangular cross-section transverse to the longitudinal axis along at least a portion of its length. The intermediate foot member 120 can be made of the same or similar materials as and constructed the same or similar to the lower foot member 110. The intermediate foot member 120 extends from a proximal end 122 downward and forward to a distal end 124. In the illustrated embodiment, the intermediate foot member 120 includes a split 126 extending along at least a portion of the length of the intermediate foot member 120 to the distal end 124. The split 126 allows medial and lateral portions of the intermediate foot member 120 to flex somewhat independently of each other. The split 126 in the intermediate foot member 120 can be aligned with the straight portion of the split 118 in the lower foot member 110. As shown in FIGS. 2A-6B, the intermediate foot member 120 can include two pads 125 on each side of the split 126. The pads 125 can cover up two cutouts in the shape of the pads 125. The cutout and the pads 125 allow the intermediate foot member 120 to be compatible with vacuum suspension systems described below. The cutouts and the pads 125 can accommodate a lever arm of a vacuum pump of the vacuum suspension systems by damping noises made by the lever arm and protecting the lever arm from wear and tear. The pads 125 can be made of a pliant or flexible (e.g., compressible) material, which is not limiting. As shown, the intermediate foot member 120 is coupled to the lower member 110 with fasteners 140, e.g., bolts, positioned proximate the distal end 124 of the intermediate foot member 120, and the lower foot member 110 extends beyond or distal to the distal end 124 of the intermediate foot member 120. In the illustrated embodiment, the distal end 124 of the intermediate foot member 120 and fasteners 140 are positioned at or near a transition between the arch region 113 and forefoot region 115 of the lower foot member 110 (e.g., proximate a portion of the foot 100, 200, 300, 400, 500, 600 generally corresponding to a metatarsal region of a natural human foot).

Figure 9:
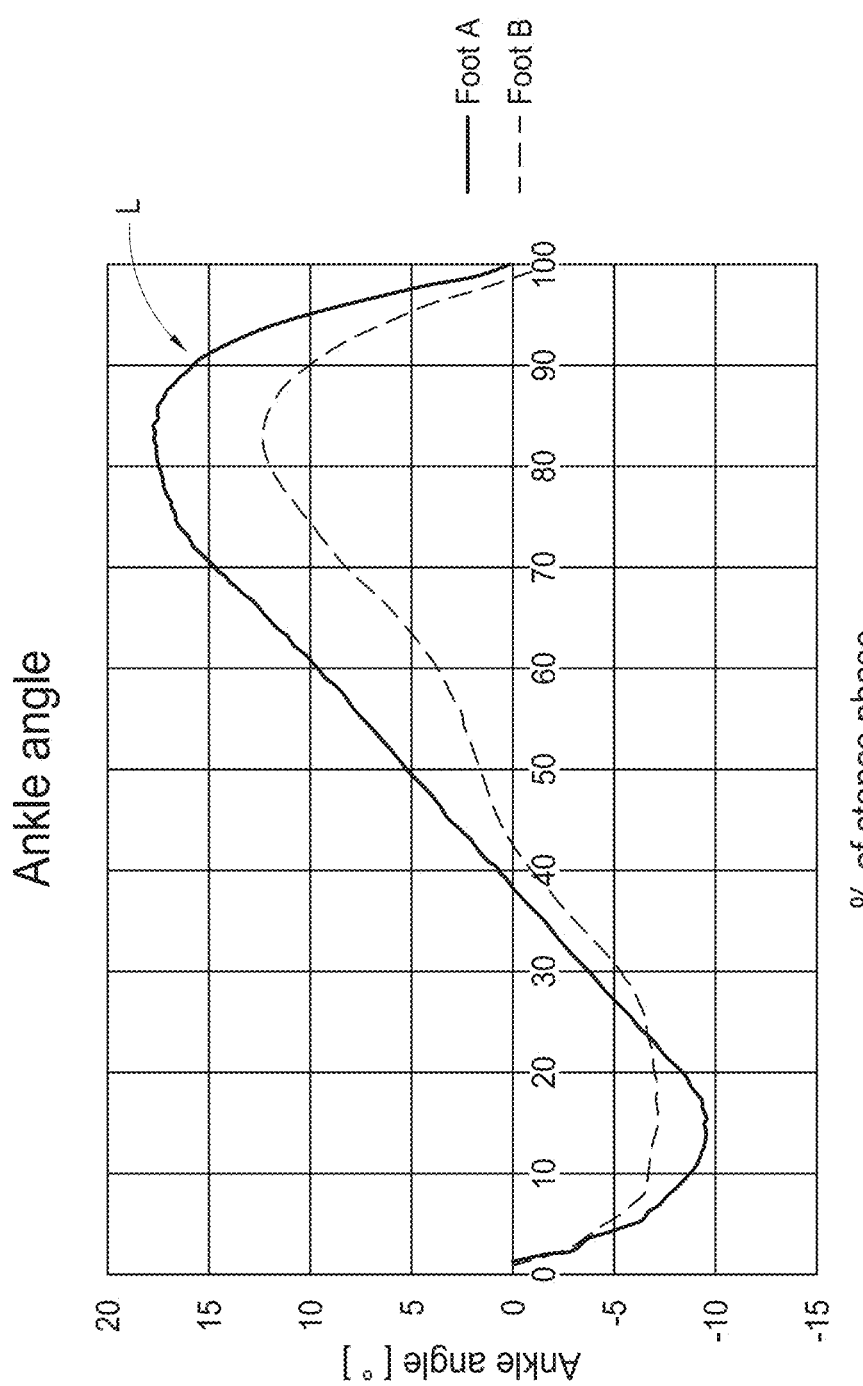
FIG. 9 illustrates a graph showing the performance of prosthetic feet according to the present disclosure compared to a conventional prosthetic foot.
Figure 10B:
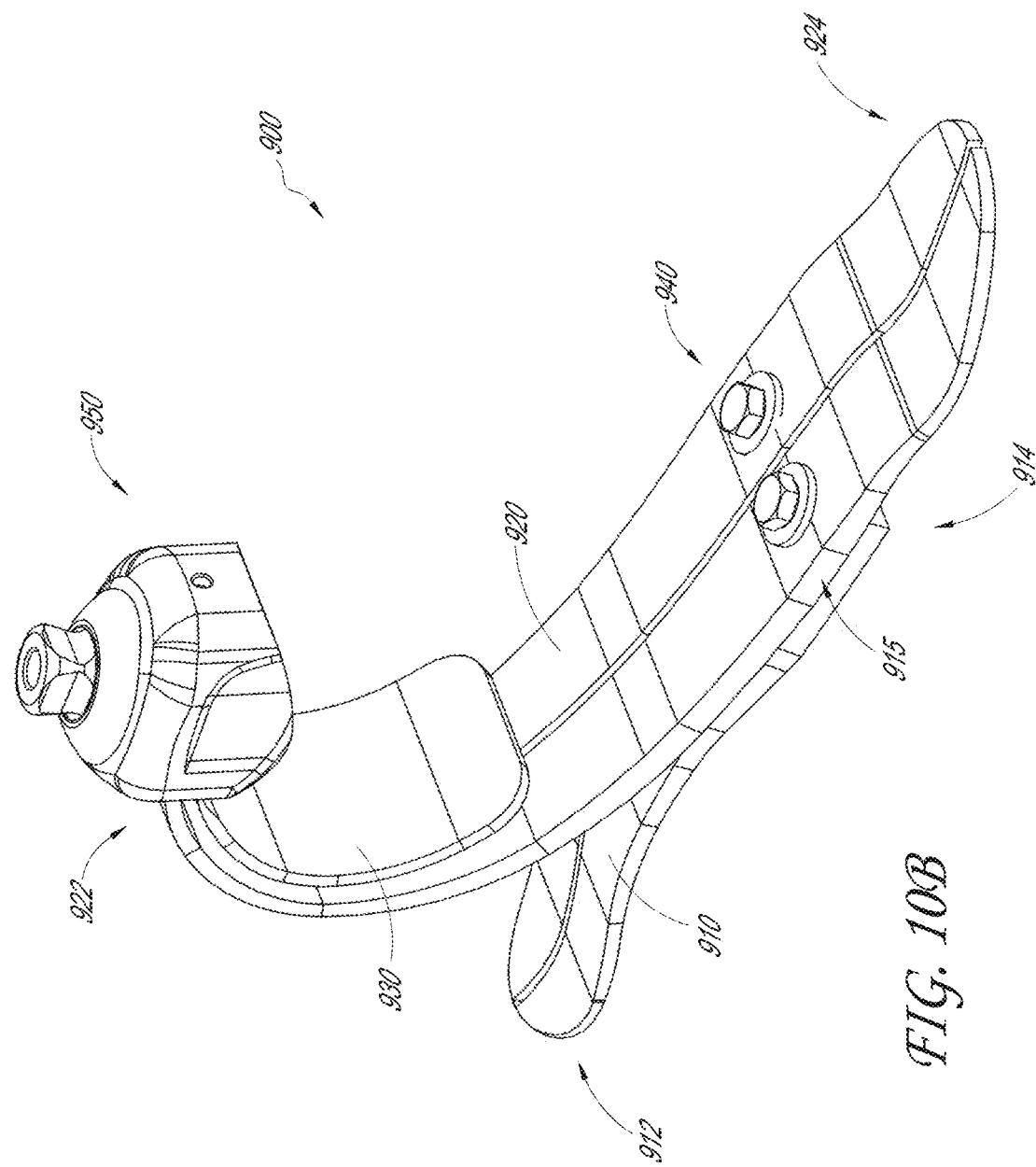

As shown, the intermediate foot member 120 tapers (e.g., gradually tapers) toward the proximal end 122 such that the distal end 124 of the intermediate foot member 120 is thicker than the proximal end 122. In previously available prosthetic feet, the center of rotation is often positioned lower and/or more anteriorly than the typical center of rotation of a natural human foot and ankle. Such feet typically flex forward of the axis of a natural human ankle, often at or near the fasteners that couple upper and lower foot members together. The taper of the intermediate foot member 120 advantageously shifts the center or axis of rotation of the foot rearward and/or closer to that of a natural human ankle. This advantageously provides for a smoother rollover. For example, FIG. 9 illustrates a graph showing the performance of prosthetic foot 100, indicated by a line "L", compared to the performance of a previously available prosthetic foot. The graph shows the ankle angle allowed by the prosthetic foot over the course of the stance phase of the gait cycle. As shown, the prosthetic foot 100 exhibits a greater range of ankle motion in the stance phase and flexes to plantarflexion earlier in the stance phase than the previously available foot. The tapered intermediate foot member 120 allows for quicker and smoother plantarflexion upon heel strike to foot flat in stance. The tapered intermediate foot member 120 also allows for greater energy storage as the foot dorsiflexes through stance to pre-toe-off, which allows for greater energy return during plantarflexion in toe-off and allows for a more controlled rollover (e.g., as evidenced by the linear trajectory shown in FIG. 9 between the beginning of dorsiflexion and the end of dorsiflexion in stance phase).

As shown in FIGS. 5A and 5B, the prosthetic foot 500 is similar to the prosthetic foot 100 in FIGS. 1A-1D except as described below. Accordingly, features of the prosthetic foot 500 can be incorporated into the prosthetic foot 100 and features of the prosthetic foot 100 can be incorporated into the prosthetic foot 500. The prosthetic foot 500 includes a shim 540 under the intermediate foot member 120. The shim is made of a material having a greater stiffness than the material of the intermediate foot member 120. In some embodiments, the shim comprises a steel plate. In some embodiments, the shim 540 is located at or near the proximal end 122 of the intermediate foot member 120. In the illustrated embodiment, a distal edge 542 of the shim 540 is aligned with a distal edge of the intermediate foot member 120. As shown in FIG. 5B, a proximal end 544 of the shim 540 can also include a split 545. The split 545 can be aligned with the split 126 in the intermediate foot member 120. The shim 540 is inserted between the intermediate foot member 120 and fasteners 154. As described below, the fasteners 154 couple an adapter 150 to the upper 130 and intermediate 120 foot members. As shown in FIG. 5B, the fasteners 154 can also couple the shim 540 to the intermediate foot member 120. The shim 540 prevents flexing of the intermediate foot member 120 where flexing is undesirable. The shim 540 also adds strength and/or rigidity to the proximal end 122 of the intermediate foot member 120.

Figure 7A:
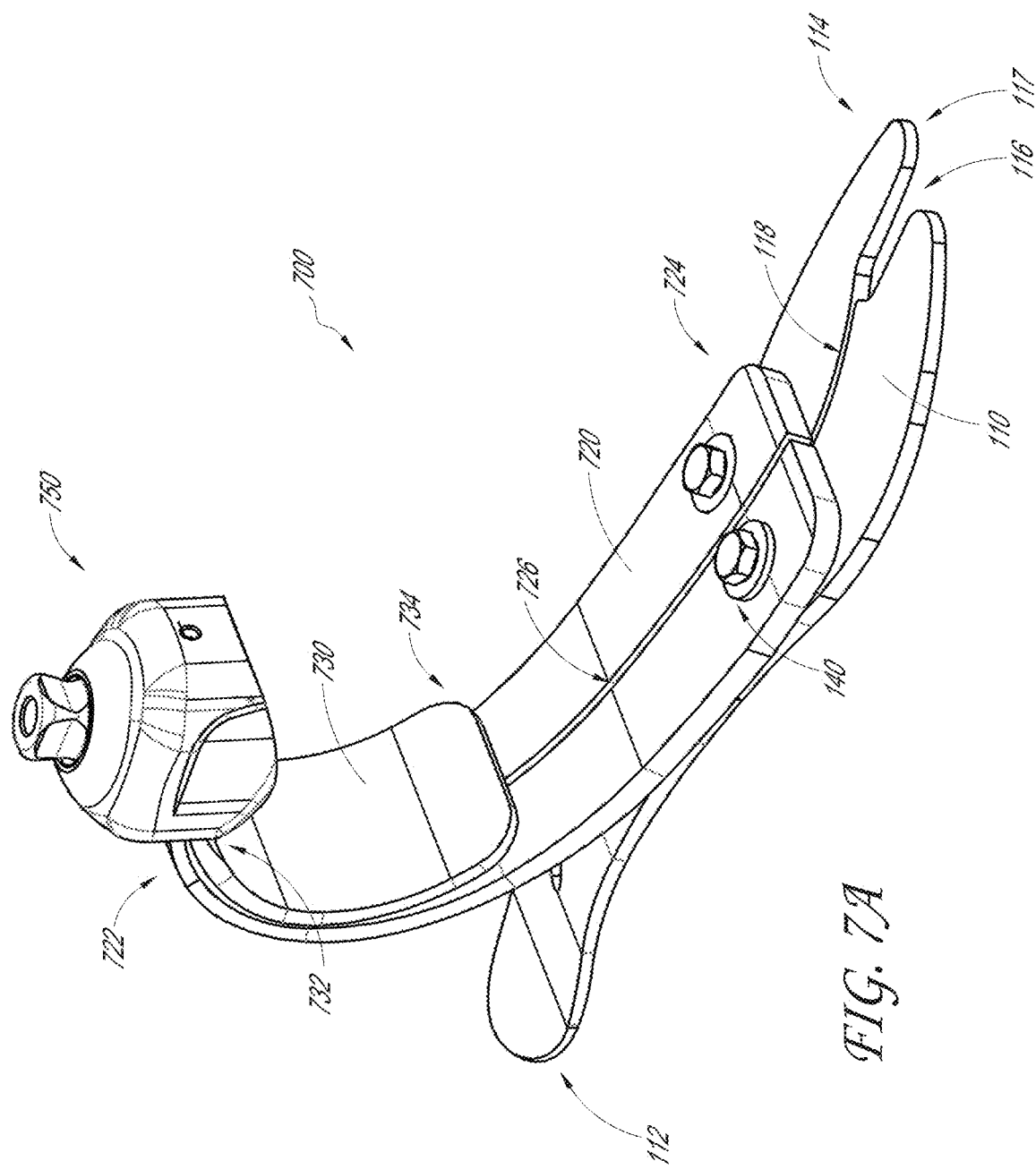
FIG. 7A illustrates a perspective view of another example embodiment of a prosthetic foot.

The prosthetic feet 700, 800 shown in the example embodiments of FIGS. 7A-8B also include tapered intermediate foot members 720, 820. As shown in FIGS. 7A-7B, the intermediate foot member 720 of the prosthetic foot 700 also extends from a proximal end 722 to a distal end 724, tapers (e.g., gradually tapers) toward the proximal end 722 such that the distal end 724 is thicker than the proximal end 722, and is coupled to the lower foot member 110 via the fasteners 140 positioned near the distal end 724 of the intermediate foot member 720 and near a transition between the arch region 113 and the forefoot region 115 of the lower foot member 110. In some embodiments, the intermediate foot member 720 includes a split 726 extending along at least a portion of the length of the intermediate foot member 720 to the distal end 724, and the split 726 can be aligned with the straight portion of the split 118 in the lower foot member 110. However, the intermediate foot member 720 of the prosthetic foot 700 is generally C-shaped or forwardly-facing concave. In the illustrated embodiment, the proximal end 722 of the intermediate foot member 720 is received in a rearwardly-facing cavity of an adapter 750. The intermediate foot member 720 extends rearwardly from the adapter 750, then curves downward and forward to the distal end 724. Additional details regarding adapter 750 and other features can be found in U.S. Publication No. 2013/0144403, which is hereby incorporated by reference herein and should be considered a part of this specification.

As shown in FIGS. 8A-8B, the intermediate foot member 820 of the prosthetic foot 800 also extends from a proximal end 822 to a distal end 824 and tapers (e.g., gradually tapers) toward the proximal end 822 such that the distal end 824 is thicker than the proximal end 822. The intermediate foot member 820 can also be coupled to the lower foot member 110 via fasteners positioned near the distal end 824 of the intermediate foot member 820 and near a transition between the arch region 113 and the forefoot region 115 of the lower foot member 110. In some embodiments, the intermediate foot member 820 also includes a split 826 extending along at least a portion of a length of the intermediate foot member 820 to the distal end 824, and the split 826 can be aligned with the straight portion of the split 118 in the lower foot member 110. However, the intermediate foot member 820 of the prosthetic foot 800 is generally J-shaped. As shown, the intermediate foot member 820 has a generally vertical proximal portion and curves forward and slightly downward to the distal end 824. An adapter 850 can be coupled to the vertical proximal portion of the intermediate foot member 820, for example, via fasteners 852, e.g., bolts, extending through the proximal portion of the intermediate foot member 820 into engagement with the adapter 850. Other shapes and configurations of tapered intermediate foot members can also be used with lower foot member 110.

Additionally, although in the illustrated embodiments the lower foot member 110 is a heel-to-toe plate and extends beyond the intermediate foot member 120, 720, 820, in other embodiments, the tapered intermediate foot member extends to a toe end, and the lower foot member is a heel plate that extends from a heel end to a proximal end that is coupled to the intermediate foot member proximal to the toe end. For example, FIGS. 10A-10D illustrate various views of an example embodiment of a prosthetic foot 900 including an intermediate foot member 920 extending from a proximal end 922 configured to be coupled to an adapter 950 to a distal toe end 924. As shown, the foot 900 also includes a heel member 910 extending from a proximal heel end 912 to a distal end 914 with an arch region 913 therebetween. As shown, the heel member 910 can be plate-like and have a rectangular transverse cross-section. The heel member 910 is coupled to the intermediate foot member 920 via fasteners 940, e.g., bolts, positioned proximate to the distal end 914 of the heel member 910, and the intermediate foot member 920 extends beyond or distal to the distal end 914 of the heel member 910. In the illustrated embodiment, the intermediate foot member 920 tapers (e.g., gradually tapers) toward both the proximal end 922 and the distal toe end 924. The intermediate foot member 920 is therefore thicker in a forefoot or metatarsal region 915 and in a region where the fasteners 940 extend through the intermediate foot member 920 than at the proximal 922 and distal 924 ends.

In the illustrated embodiment, the intermediate foot member 920, e.g., at least a proximal portion of the intermediate foot member 920, is generally C-shaped. However, in other embodiments, an intermediate foot member that extends from a proximal end configured to be coupled to an adapter to a toe end and is tapered toward both the proximal and distal toe ends can be J-shaped or L-shaped, extending from the proximal end downward and forward to the distal end (similar to the intermediate foot member 820), or have other shapes and configurations. In the illustrated embodiment, the intermediate foot member 920 includes a change in curvature 925 distal to the forefoot region 915 to define a toe portion that is vertically downwardly offset from the remainder of the intermediate foot member 920 proximal to the change in curvature 925. The change in curvature 925 can advantageously allow the foot 900 to be supported at or near the heel and toe when resting on a support surface rather than at the heel and the fasteners 940. This allows for enhanced suspension and increased vertical displacement of the foot 900 during stance because the fasteners are not in contact with the ground. Additional details regarding drop-toe or vertically offset toe portions can be found in U.S. Publication No. 2013/0144403, the entirety of which is hereby incorporated herein by reference and should be considered a part of this specification. However, in other embodiments, the intermediate foot member 920, or another embodiment of an intermediate foot member that extends from a proximal end configured to be coupled to an adapter to a toe end and is tapered toward both the proximal and distal toe ends need not include such a change in curvature.

In the illustrated embodiments, the prosthetic feet 100, 200, 300, 400, 500, 600, 700, 800, 900 also include an upper foot member 130, 230, 330, 430, 630, 730, 830, 930 respectively. However, the upper foot member 130, 230, 330, 430, 630, 730, 830, 930 is optional and need not be included in other embodiments. As shown in FIGS. 1A-1D and 5A-5B, the upper foot member 130 extends from a proximal end 132 to a distal end 134 and is tapered (e.g., gradually tapers) toward the distal end 134 such that the distal end 134 is thinner than the proximal end 132. In the illustrated embodiment, there is a gap 136 between the distal end 134 of the upper foot member 130 and a top surface of the intermediate foot member 120. During the mid-stance and toe-off phases of the gait cycle, the gap 136 closes and the upper foot member 130 engages the intermediate foot member 120, which increases the stiffness of the foot 100 and/or stores additional energy in the intermediate foot member 120 as the foot 100 moves toward toe-off. In some embodiments the gap 136 gradually closes providing progressive stiffening of the foot during mid-stance and toe-off. The upper foot member 130 engages the intermediate foot member 120 when the prosthetic foot 100 is placed under load and advantageously provides support for the foot 100 when under a relatively high load. In some embodiments, the upper foot member 130 can be designed and/or selected for a particular user and/or activity so that the upper foot member 130 engages the intermediate foot member 120 under a specific load and provides a desired resistance to achieve a desired stiffness curve or performance for the foot 100. The upper foot member 130 can therefore provide for dynamic control under load.

Figure 2B:
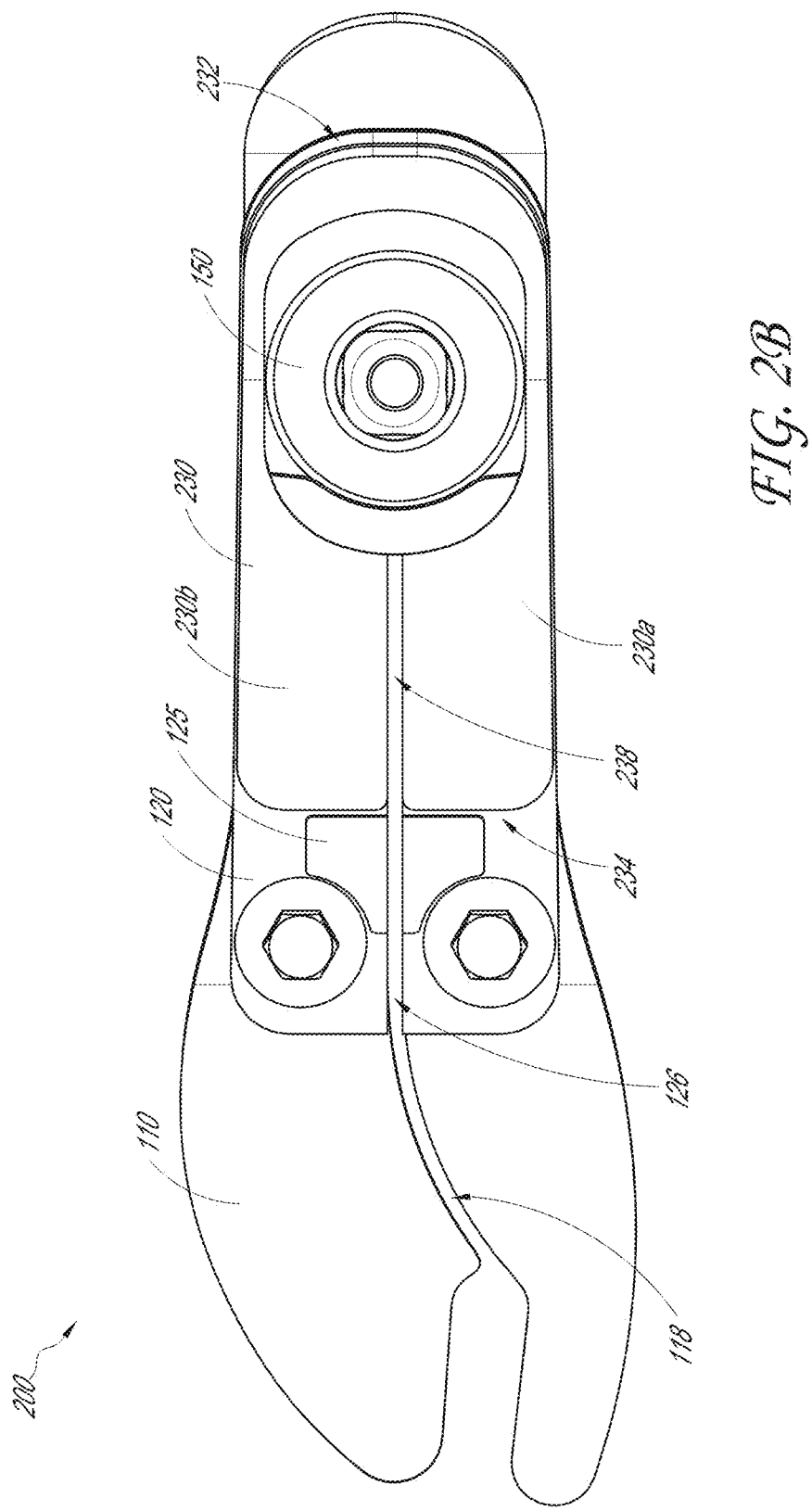
FIG. 2B illustrates a top view of the prosthetic foot of FIG. 2A.
Figure 6A:
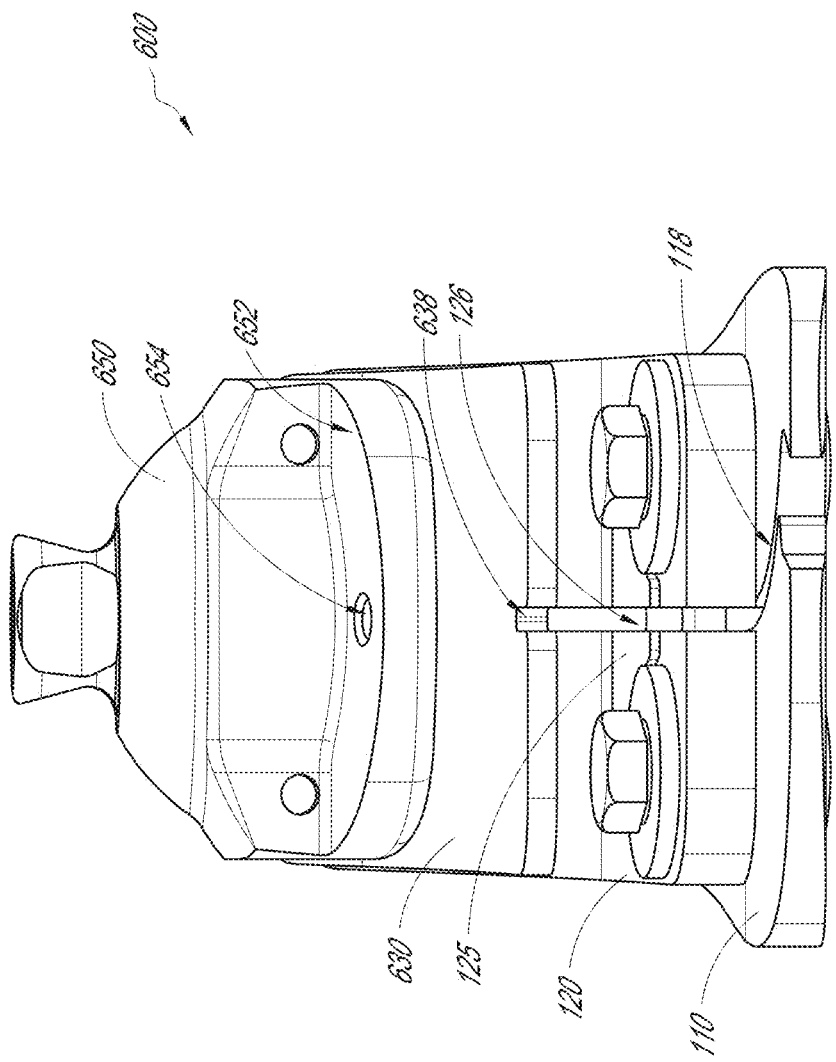
FIG. 6A illustrates a front view of another example embodiment of a prosthetic foot.
Figure 6B:
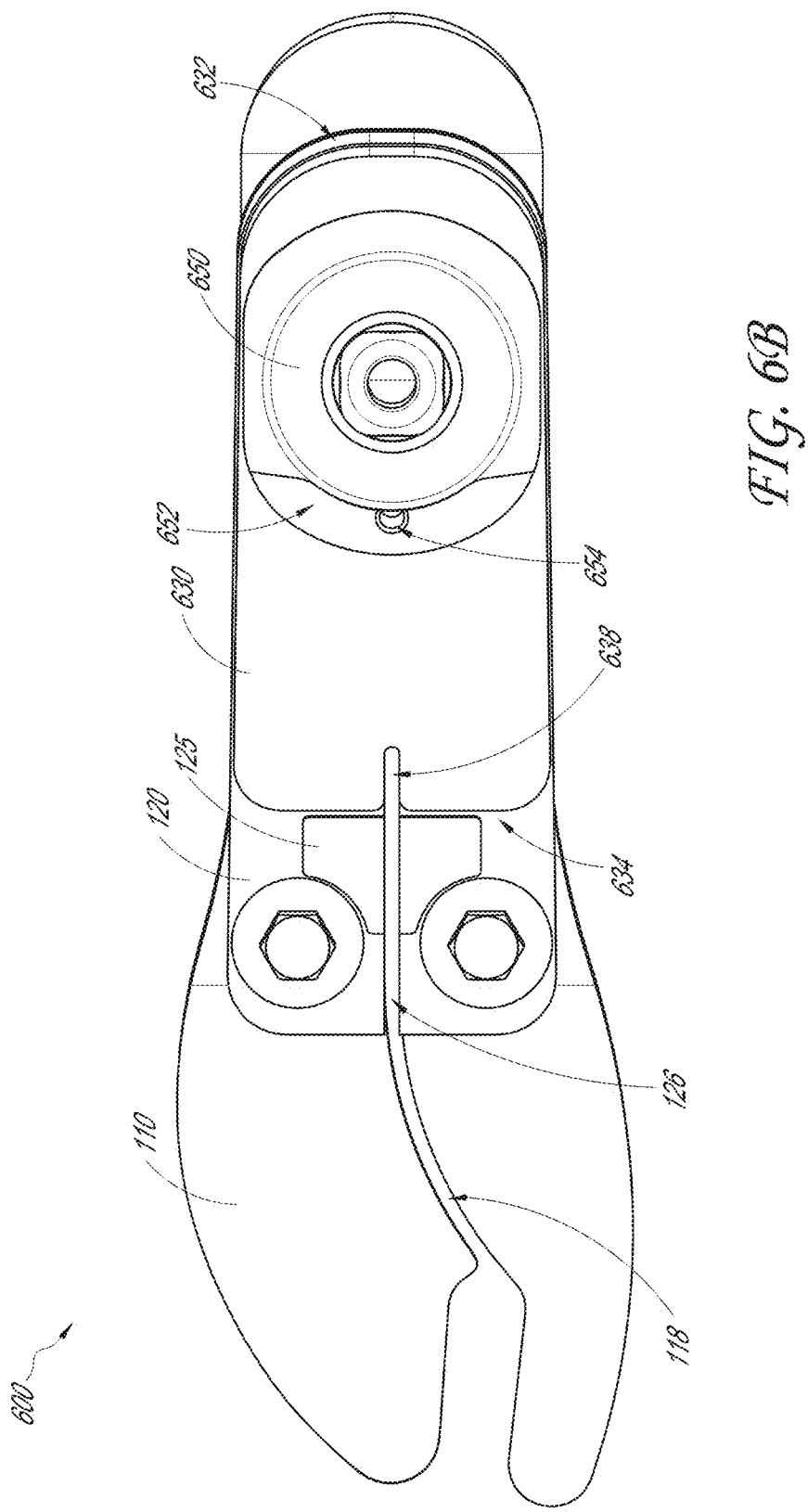
FIG. 6B illustrates a top view of the prosthetic foot of FIG. 6A.

As shown in FIGS. 2A-2B, the upper foot member 230 is similar to the upper foot member 130 in FIGS. 1A-1D and 5A-5B except as described below. Accordingly, features of the upper foot member 230 can be incorporated into the upper foot member 130 and features of the upper foot member 130 can be incorporated into the upper foot member 230. The upper foot member 230 includes a split 238 extending along at least a portion of the length of the upper foot member 230 from a distal end 234 toward a proximal end 232. In the illustrated embodiments, the split 238 extends from the distal end 234 and ends proximate the adapter 150 that is on top of the upper foot member 230. The split 238 allows medial 230a and lateral 230b portions of the upper foot member 230 to flex somewhat independently of each other. The split 238 in the upper foot member 230 can optionally be aligned with the split 126 in the intermediate foot member 120. The split 226 in the upper foot member 230 can also optionally be aligned with the straight portion of the split 118 in the lower foot member 110. FIGS. 6A-6B illustrates the upper foot member 630 that also has a split 638 near or along the longitudinal axis of the foot 600. The split 638 also can extend from the distal end 634 toward the proximal end 632 of the upper foot member 630. In some embodiments, the split is about 2 mm-10 mm in length. In some embodiments, the split does not extend proximate an adapter, but ends between the distal end and the adapter. In some embodiments, the split extends through the entire upper foot plate 630 so that the upper foot plate 620 is formed by a lateral portion and a medial portion. The lateral and medial portions can advantageously have different functional characteristics or appearances. As shown, the length of the split on the upper foot member can be varied for a particular user and/or activity so that a portion of the upper foot member near the distal end can flex somewhat independently, thereby providing a smoother rollover for the particular user and/or activity.

FIGS. 11A-11B show a prosthetic foot 1100 that is similar to the prosthetic foot 100 in FIGS. 1A-1D, except as described below. Accordingly, features of the prosthetic foot 1100 can be incorporated into the prosthetic foot 100, and features of the prosthetic foot 100 can be incorporated into the prosthetic foot 1100. As shown in FIGS. 11A-11B, the upper foot member 1130 is similar to the upper foot member 130 in FIGS. 1A-1D and 5A-5B and the upper foot member 630 in FIG. 6A-6B except as described below. Accordingly, features of the upper foot member 1130 can be incorporated into the upper foot member 130, 630 and features of the upper foot member 130, 630 can be incorporated into the upper foot member 1130. The upper foot member 1130 extends from a proximal end 1132 to a distal end 1134 and is tapered (e.g., gradually tapers) toward the proximal end 1132 such that the proximal end 1132 is thinner than the distal end 1134. In the illustrated embodiment, there is also a gap 1136 between the distal end 1134 of the upper foot member 1130 and a top surface of the intermediate foot member 120. During the mid-stance and toe-off phases of the gait cycle, the gap 1136 can close and the upper foot member 1310 can engage the intermediate foot member 120, which increases the stiffness of the foot 1100 and/or stores additional energy in the intermediate foot member 120 as the foot 1100 moves toward toe-off. The gap 1136 can gradually close providing progressive stiffening of the foot during mid-stance and toe-off. The upper foot member 1130 can also engage the intermediate foot member 120 when the prosthetic foot 1100 is placed under load and advantageously provides support for the foot 1100 when under a relatively high load. In some embodiments, thickness of the distal end 1134 of the upper foot member 1130 can vary. For example, the thickness of the distal end 1134 can be increased to decrease the gap 1136 between the intermediate foot member 120 and the upper foot member 1130 to control the amount of bending of the intermediate foot member 120. The upper foot member 1130 can thus advantageously allow the same mold of the intermediate foot member 120 to be used while also allowing engagement between the upper foot member 1130 and the intermediate foot member 120 to provide a desired resistance to achieve a desired stiffness curve or performance for the foot 1100.

Figure 3B:
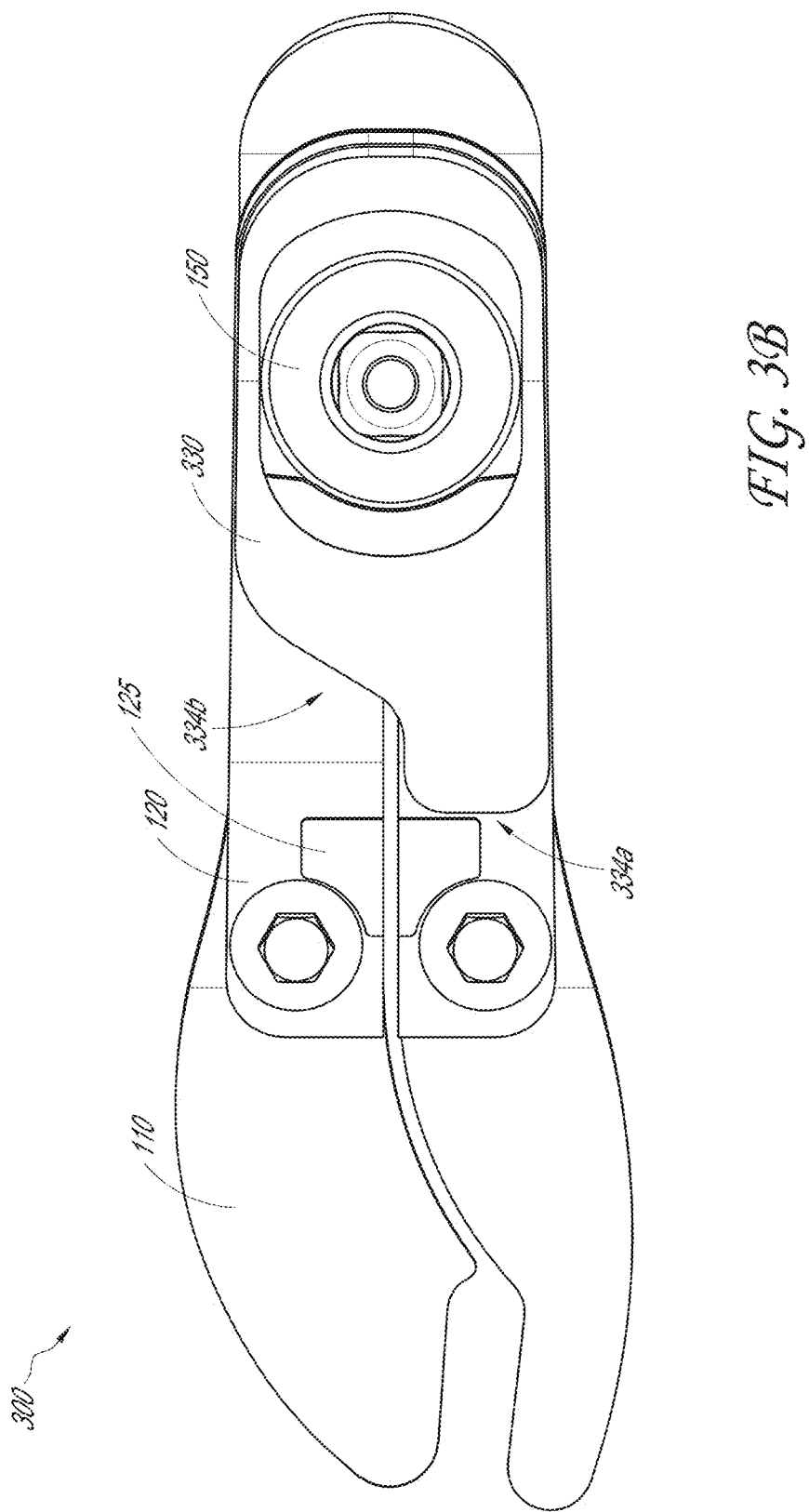
FIG. 3B illustrates a top view of the prosthetic foot of FIG. 3A.

FIGS. 3A-3B illustrate another example embodiment of the upper foot member 330. The upper foot member 330 is similar to the upper foot member 130 in FIGS. 1A-1D and 5A-5B and the upper foot member 230 in FIGS. 2A-2B except as described below. Accordingly, features of the upper foot member 330 can be incorporated into the upper foot members 130, 230 and features of the upper foot member 130, 230 can be incorporated into the upper foot member 330. The upper foot member 330 is asymmetric with respect to a longitudinal axis of the foot 300 along at least a portion of its length. In some embodiments, a distal end 334a of the upper foot member 330 on a medial side of the longitudinal axis of the foot 300 extends beyond or distal of a distal end 334b of the upper foot member 300 on a lateral side of the longitudinal axis of the foot 300. In other words, the upper foot member 300 is longer on the medial side of the longitudinal axis of the foot 300 than on the lateral side of the longitudinal axis of the foot 300. In some embodiments, transition from the distal end 334a to the distal end 334b is a "step-like" or discontinuous change. In other embodiments, the distal end 334a can more gradually transition to the distal end 334b. As shown, there is a gap 336 between the distal ends 334a, 334b of the upper foot member 330 and the top surface of the intermediate foot member 120. The asymmetry of the upper foot member 300 provides greater stiffness to the medial side longitudinal axis of the foot 300 and/or stores more energy in the intermediate foot member 120 on the medial side of longitudinal axis of the foot 300 as the foot 300 moves toward toe-off. In some embodiments, after the gap 336 closes on the lateral side of the longitudinal axis of the foot 300, the gap 336 continues to gradually close on the medial side of the longitudinal axis of the foot 300 during mid-stance and toe-off, providing a smoother rollover.

Figure 4A:
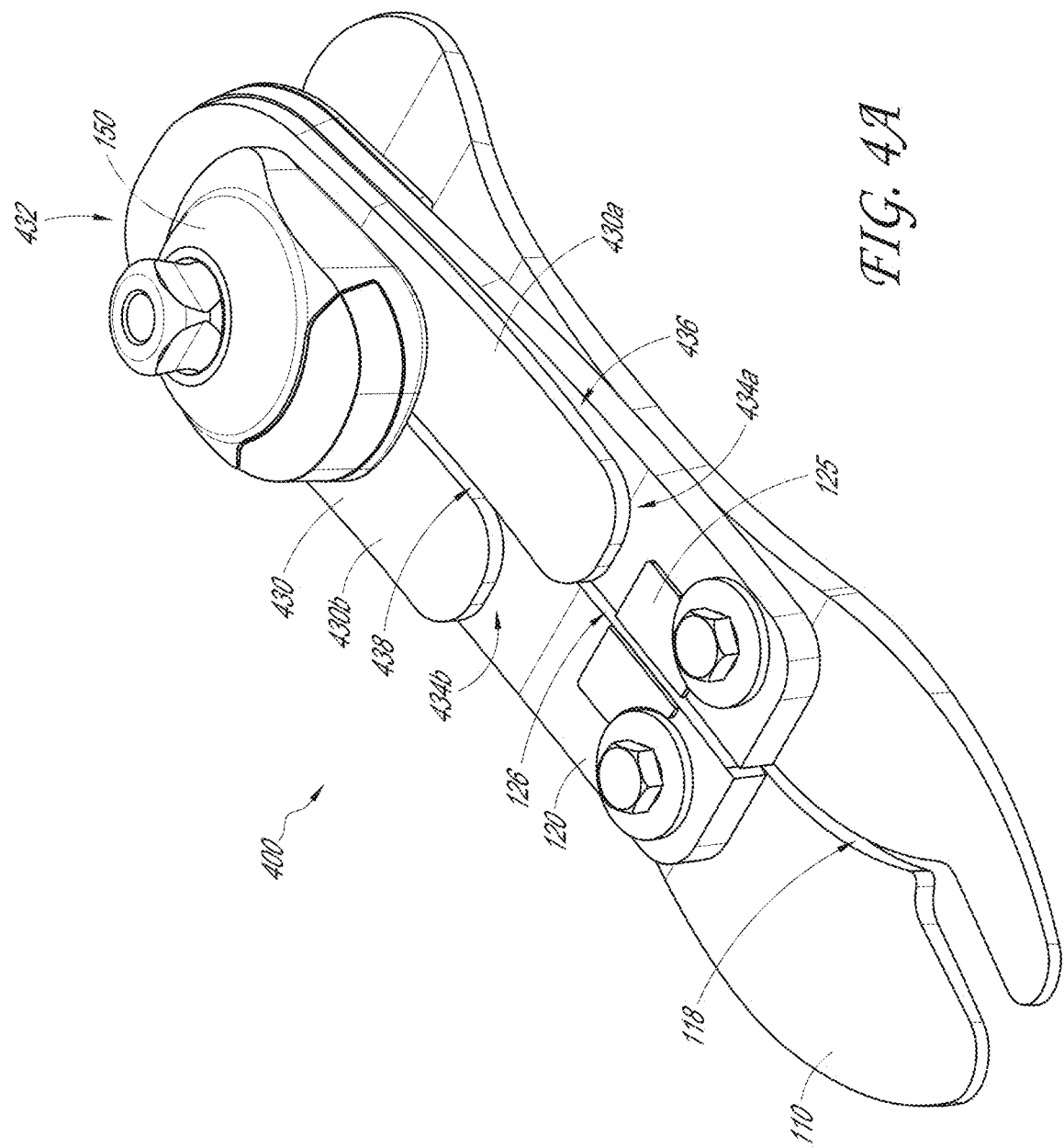
FIG. 4A illustrates a perspective view of another example embodiment of a prosthetic foot.
Figure 4B:
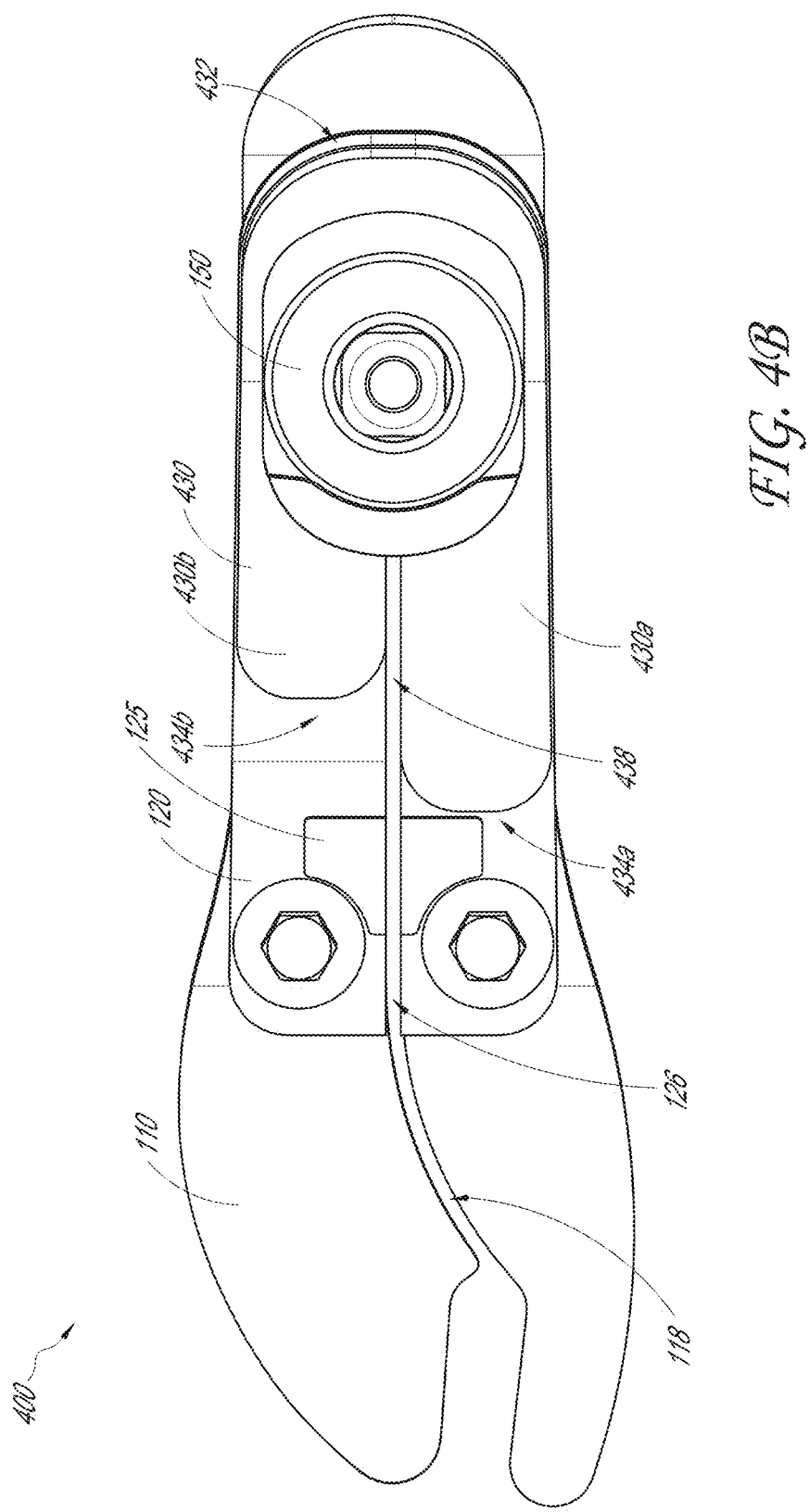
FIG. 4B illustrates a top view of the prosthetic foot of FIG. 4A.

FIGS. 4A-4B illustrate another example embodiment of the upper foot member 430. The upper foot member 430 is similar to the upper foot member 130 in FIGS. 1A-1D and 5A-5B, the upper foot member 230 in FIG. 2A-2B and the upper foot member 330 in FIG. 3A-3B except as described below. Accordingly, features of the upper foot member 430 can be incorporated into the upper foot members 130, 230, 330 and features of the upper foot member 130, 230, 330 can be incorporated into the upper foot member 430. The upper foot member 430 is asymmetric with respect to a longitudinal axis of the foot 400 along at least a portion of its length. In some embodiments, a distal end 434a of the upper foot member 430 on a medial side of the longitudinal axis of the foot 400 extends beyond or distal of a distal end 434b of the upper foot member 400 on a lateral side of the longitudinal axis of the foot 400. In other words, the upper foot member 400 is longer on the medial side of the longitudinal axis of the foot 400 than on the lateral side of the longitudinal axis of the foot 400. In some embodiments, transition from the distal end 434a to the distal end 434b is a "step-like" or discontinuous change. In other embodiments, the distal end 434a can more gradually transit to the distal end 434b. There is a gap 436 between the distal ends 434a, 434b of the upper foot member 430 and the top surface of the intermediate foot member 120. The upper foot member 430 also includes a split 438 extending along at least a portion of the length of the upper foot member 430 from the distal end 434b toward a proximal end 432. In the illustrated embodiments, the split 238 extends from the distal end 234b and ends proximate the adapter 150 that is on top of the upper foot member 430. The split 438 in the upper foot member 430 can optionally be aligned with the split 126 in the intermediate foot member 120. The split 438 in the upper foot member 430 can also optionally be aligned with the straight portion of the split 118 in the lower foot member 110. The asymmetry of the upper foot member 400 provides greater stiffness to the medial side longitudinal axis of the foot 400 and/or stores more energy in the intermediate foot member 120 on the medial side of longitudinal axis of the foot 400 as the foot 400 moves toward toe-off. The split 426 allows medial 430a and lateral 430b portions of the upper foot member 430 to flex somewhat independently of each other.

As shown in FIGS. 7A-7B, the upper foot member 730 of foot 700 is generally C-shaped to correspond to the shape of the intermediate foot member 720 and tapers (e.g., gradually tapers) toward the distal end of the upper foot member 730. In the illustrated embodiment, the proximal end 732 of the upper foot member 730 is received in the cavity of the adapter 750. A gap 736 between the upper foot member 730 and intermediate foot member 720 extends from near the proximal end of the upper foot member 730 to the distal end of the upper foot member 730. The gap 736 can close and the upper foot member 730 can engage the intermediate foot member 720 during mid-stance and toe-off to advantageously increase the stiffness of the foot 700 and/or store additional energy in the intermediate foot member 720 as the foot 700 moves toward toe-off. As shown in FIGS. 10A-10D, the upper foot member 930 of foot 900 is similarly generally C-shaped to correspond to the shape of the intermediate foot member 920. The upper foot member 930 can taper (e.g., gradually taper) toward the distal end of the upper foot member 930 in some embodiments.

As shown in FIGS. 8A-8B, the upper foot member 830 of foot 800 is generally J-shaped to correspond to the shape of the intermediate foot member 820. In the illustrated embodiment, the proximal end 832 of the upper foot member 830 is positioned between the intermediate foot member 820 and the adapter 850 and secured to the intermediate foot member 820 and adapter 850 via the fasteners 852. The upper foot member 830 includes a generally vertical proximal portion and curves forward and slightly downward to the distal end 834. As shown, there is a gap 836 between the curved portion of the upper foot member 830 and the intermediate foot member 820. The gap 836 closes and the upper foot member 830 engages the intermediate foot member 820 during mid-stance and toe-off to increase the stiffness of the foot 800 and/or store additional energy in the intermediate foot member 820 as the foot 800 moves toward toe-off.

As shown in FIGS. 1A-6B, the adapter 150 is configured to couple the prosthetic foot 100, 200, 300, 400, 500 to the user's residual limb or another prosthetic component. Additional details on example embodiments of adapters that can be used with prosthetic feet according to the present disclosure can be found in U.S. Pat. No. 8,007,544, which is hereby incorporated by reference herein and should be considered a part of this specification. In the illustrated embodiment, the adapter 150 is placed adjacent the top surface of the upper foot member 130, 230, 330, 430 at or near the proximal end 132, 232, 332, 432 of the upper foot member 130, 230, 330, 430 and coupled to the upper foot members 130, 230, 330, 430 and the intermediate foot member 120 via fasteners 154. However, in other embodiments not including an upper foot member 130, 230, 330, 430, the adapter 150 can be placed adjacent and coupled to the intermediate foot member 120.

FIGS. 6A and 6B illustrate the adapter 650, which is similar to the adapter 150 as described below. Accordingly, features of the adapter 150 can be incorporated into the adapter 650 and features of the adapter 650 can be incorporated into the adapter 150 used with other embodiments disclosed herein. The adapter 650 includes a cut-out feature 652. The cut-out feature 652 allows the prosthetic foot 600 to be compatible with vacuum suspension systems. Further, any embodiments shown and described herein can be configured to be compatible with vacuum suspension systems. Such a system generates negative pressure within a prosthetic socket to improve the fit and stability of a prosthetic socket relative to a residual limb. The distal end of the residual limb typically has more soft tissue compared to an area closer to the knee. The distal end is therefore more susceptible to volume fluctuations throughout the day, which can impede stabilization and suspension of the socket. A vacuum suspension system that can be used with the feet described herein can therefore apply a vacuum to the distal end of the residual limb to improve stability and suspension. The system can include a frame coupled to the foot and a membrane disposed on or between parts of the frame. When the user places weight on the heel of the foot, the membrane expands, which causes air to be drawn out of the socket to create and maintain the vacuum. Additional details regarding such systems are shown and described in U.S. Publications 2013/0289742, 2013/0289741, and 2013/0221544 and U.S. Design Pat. Nos. D711,510 and D718,861, which are incorporated by reference herein in their entirety and should be considered a part of this specification. When the adapter 650 is not used with vacuum suspension systems, the cut-out feature 652 can be optionally covered with a plastic cover (not shown in FIGS. 6A and 6B) similar to a plastic cover 152 of the adapter 150 shown in FIG. 2A. The plastic cover can protect vacuum suspension system connecting features, such as a connection port 654, that can be located on the cut-out-feature 652. For example, the plastic cover 152 can prevent dirt and dust from clogging the connection port 654. The plastic cover 152 can also prevent tempering of the connection port 654. Further, the plastic cover 152 can make the adapter 650 have an appearance of the adapter 150 when the adapter 650 is not used with vacuum suspension systems.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
   an adapter configured to couple the prosthetic foot to a user's residual limb or another prosthetic component;
   a first elongate foot member extending from a proximal end to a distal end, a proximal portion of the first elongate foot member coupled to the adapter, wherein the proximal portion of the first elongate foot member is adjacent to a bottom surface of the adapter; and
   a second elongate foot member extending from a proximal end to a distal end, a proximal portion of the second elongate foot member coupled to the proximal portion of the first elongate foot member and the adapter with the proximal portion of the first elongate foot member located between the bottom surface of the adapter and the proximal portion of the second elongate foot member, wherein the second elongate foot member comprises a taper such that a thickness of the second elongate foot member increases toward the distal end of the second elongate foot member,
   wherein a gap separates the distal end of the first elongate foot member from the second elongate foot member when the prosthetic foot is at rest on a support surface, and wherein the gap closes during dorsiflexion to increase an amount of energy stored in the second elongate foot member as the prosthetic foot moves toward toe-off.

2. The prosthetic foot of claim 1, wherein the first elongate foot member comprises a taper such that a thickness of the first elongate foot member increases toward the proximal end of the first elongate foot member.

3. The prosthetic foot of claim 1, wherein the distal end of the first elongate foot member engages the second elongate foot member during load to provide dynamic stiffness control.

4. The prosthetic foot of claim 3, wherein an entirety of the first elongate member contacts the second elongate foot member when the gap completely closes during load.

5. The prosthetic foot of claim 1, wherein the distal end of the first elongate foot member terminates proximal of the distal end of the second elongate foot member.

6. The prosthetic foot of claim 1, wherein the taper of the second elongate foot member shifts a center of rotation of the prosthetic foot rearward toward a location corresponding to a center of rotation of a natural human ankle.

7. The prosthetic foot of claim 1, comprising a third elongate foot member extending from a proximal end to a distal end, the third elongate foot member located below the second elongate foot member when the prosthetic foot is at rest on a support surface, the third elongate foot member being coupled to the second elongate foot member proximate the distal end of the second elongate foot member and proximal of the distal end of the third elongate foot member.

8. The prosthetic foot of claim 1, further comprising a shim disposed below the second elongate foot member and coupled to the second elongate foot member proximate the proximal end of the first elongate foot member.

9. A prosthetic foot comprising:
   an adapter configured to couple the prosthetic foot to a user's residual limb or another prosthetic component, the adapter further comprising a removable cover configured to be disposed over a connector on the adapter when the connector is not in use;
   a first elongate foot member extending from a proximal end to a distal end, a proximal portion of the first elongate foot member coupled to the adapter, wherein the proximal portion of the first elongate foot member is adjacent to a bottom surface of the adapter; and
   a second elongate foot member extending from a proximal end to a distal end, a proximal portion of the second elongate foot member coupled to the proximal portion of the first elongate foot member and the adapter with the proximal portion of the first elongate foot member located between the bottom surface of the adapter and the proximal portion of the second elongate foot member, wherein when the prosthetic foot is at rest on a support surface, the adapter is located above the first elongate foot member and the first elongate foot member is located above the second elongate foot member,
   wherein a gap separates the distal end of the first elongate foot member from the second elongate foot member when the prosthetic foot is at rest on a support surface, and wherein the gap closes during dorsiflexion to increase an amount of energy stored in the second elongate foot member as the prosthetic foot moves toward toe-off.

10. The prosthetic foot of claim 9, wherein the second elongate foot member comprises a taper such that a thickness of the second elongate foot member increases toward the distal end of the second elongate foot member.

11. The prosthetic foot of claim 10, wherein the first elongate foot member comprises a taper such that a thickness of the first elongate foot member increases toward the proximal end of the first elongate foot member.

12. The prosthetic foot of claim 9, wherein the connector comprises a connecting port configured for use with a vacuum suspension system.

13. The prosthetic foot of claim 12, wherein the connector is located on a recessed portion of the adapter, the recessed portion configured to allow the prosthetic foot to be compatible with the vacuum suspension system.

14. The prosthetic foot of claim 9, wherein the adapter comprises a pyramid adapter and the connector is located on the adapter distally of the pyramid.

15. The prosthetic foot of claim 9, comprising a gap between a curved bottom surface of the adapter and a top surface of the first elongate foot member.

16. The prosthetic foot of claim 9, wherein the removable cover comprises a plastic cover.

17. The prosthetic foot of claim 9, comprising a third elongate foot member extending from a proximal end to a distal end, the third elongate foot member located below the second elongate foot member when the prosthetic foot is at rest on a support surface, the third elongate foot member being coupled to the second elongate foot member proximate the distal end of the second elongate foot member and proximal of the distal end of the third elongate foot member.

18. The prosthetic foot of claim 9, wherein the distal end of the first elongate foot member terminates proximal of the distal end of the second elongate foot member.

19. The prosthetic foot of claim 9, wherein the distal end of the first elongate foot member engages the second elongate foot member during load to provide dynamic stiffness control.

20. The prosthetic foot of claim 19, wherein an entirety of the first elongate member contacts the second elongate foot member when the gap completely closes during load.

* * * * *